US012618087B2

(12) United States Patent
Kim et al.

(10) Patent No.: US 12,618,087 B2
(45) Date of Patent: May 5, 2026

(54) THRAUSTOCHYTRID STRAIN GENETICALLY ENGINEERED FOR THE PRODUCTION OF BIOMATERIALS INCLUDING LONG-CHAIN POLYUNSATURATED FATTY ACIDS

(71) Applicants: PHYCOIL BIOTECHNOLOGY INTERNATIONAL, INC., Fremont, CA (US); PHYCOILBIOTECH KOREA, Inc., Seoul (KR)

(72) Inventors: Jane Kim, Fremont, CA (US); Riyaz Bhat, Fremont, CA (US); Jeffrey Moseley, Fremont, CA (US); Chungsoon Im, Fremont, CA (US)

(73) Assignee: Phycoil Biotechnology International, Inc., Fremont, CA (US)

( * ) Notice: Subject to any disclaimer, the term of this patent is extended or adjusted under 35 U.S.C. 154(b) by 461 days.

(21) Appl. No.: 18/155,191

(22) Filed: Jan. 17, 2023

(65) Prior Publication Data

US 2023/0265470 A1 Aug. 24, 2023

Related U.S. Application Data

(60) Provisional application No. 63/300,101, filed on Jan. 17, 2022.

(51) Int. Cl.
| | |
|---|---|
| *C12P 7/6427* | (2022.01) |
| *A23K 20/158* | (2016.01) |
| *C12P 7/6472* | (2022.01) |

(52) U.S. Cl.
CPC .......... *C12P 7/6427* (2013.01); *A23K 20/158* (2016.05); *C12P 7/6472* (2013.01)

(58) Field of Classification Search
None
See application file for complete search history.

(56) References Cited

U.S. PATENT DOCUMENTS

| | | | |
|---|---|---|---|
| 9,932,554 B2 | 4/2018 | Im et al. | |
| 2011/0177031 A1* | 7/2011 | Apt | A23L 33/40 435/243 |
| 2012/0171733 A1* | 7/2012 | Im | C12N 1/12 435/166 |
| 2016/0319218 A1 | 11/2016 | Leininger et al. | |

FOREIGN PATENT DOCUMENTS

| | | |
|---|---|---|
| KR | 10-2018-0028288 | 3/2018 |
| KR | 10-1946362 | 2/2019 |
| KR | 10-2020-0074047 | 6/2020 |

OTHER PUBLICATIONS

KIPO, PCT Search Report & Written Opinion of PCT/IB2023/050385 dated Apr. 17, 2023.

* cited by examiner

*Primary Examiner* — Christian L Fronda
(74) *Attorney, Agent, or Firm* — HelixIP LLP

(57) ABSTRACT

Provided herein are microorganism of a Thraustochytrid and a method for preparing bio-oil using the same, and more particularly, *Schizochytrium* sp. PB31 (PTA-123692) having bio-oil producibility, and a method of preparing bio-oil, particularly bio-oil having a content of omega-3 and/or 6 long-chain polyunsaturated fatty acids of 30% or more by weight or more based on total fatty acids, characterized by culturing the microorganism.

20 Claims, 11 Drawing Sheets

Specification includes a Sequence Listing.

【FIG. 1】
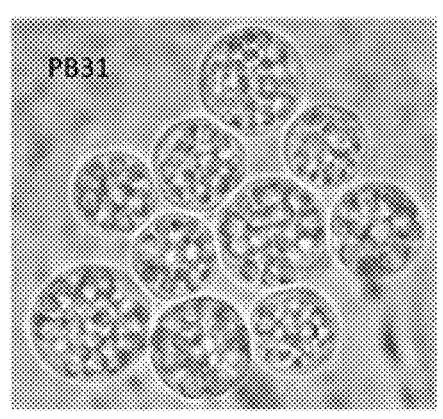
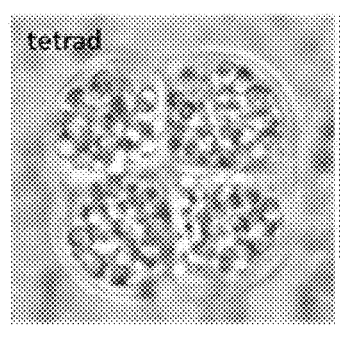
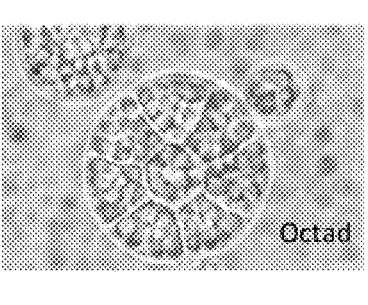
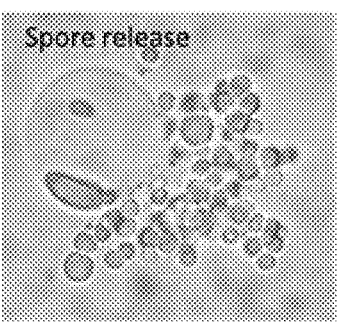
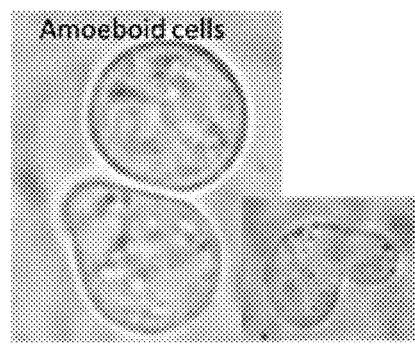
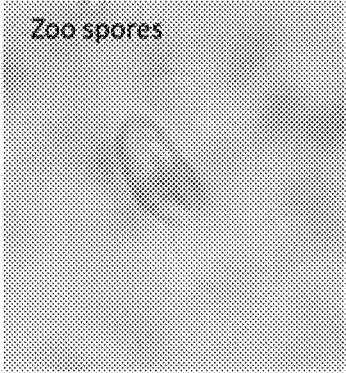
Amoeboid cells
Pictures for paper PB31
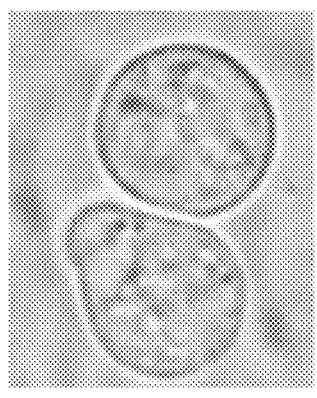
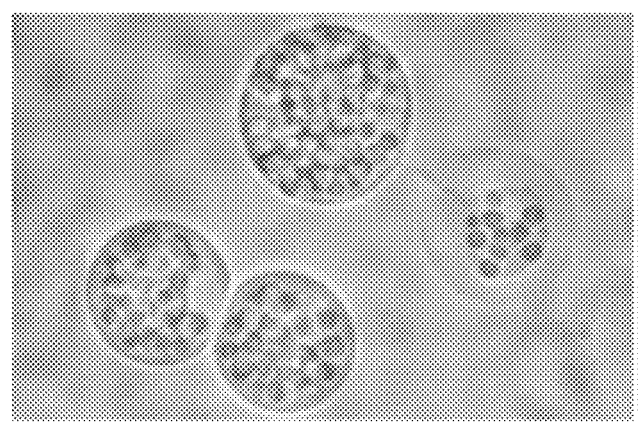
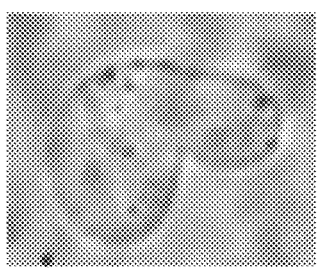

【FIG. 2】
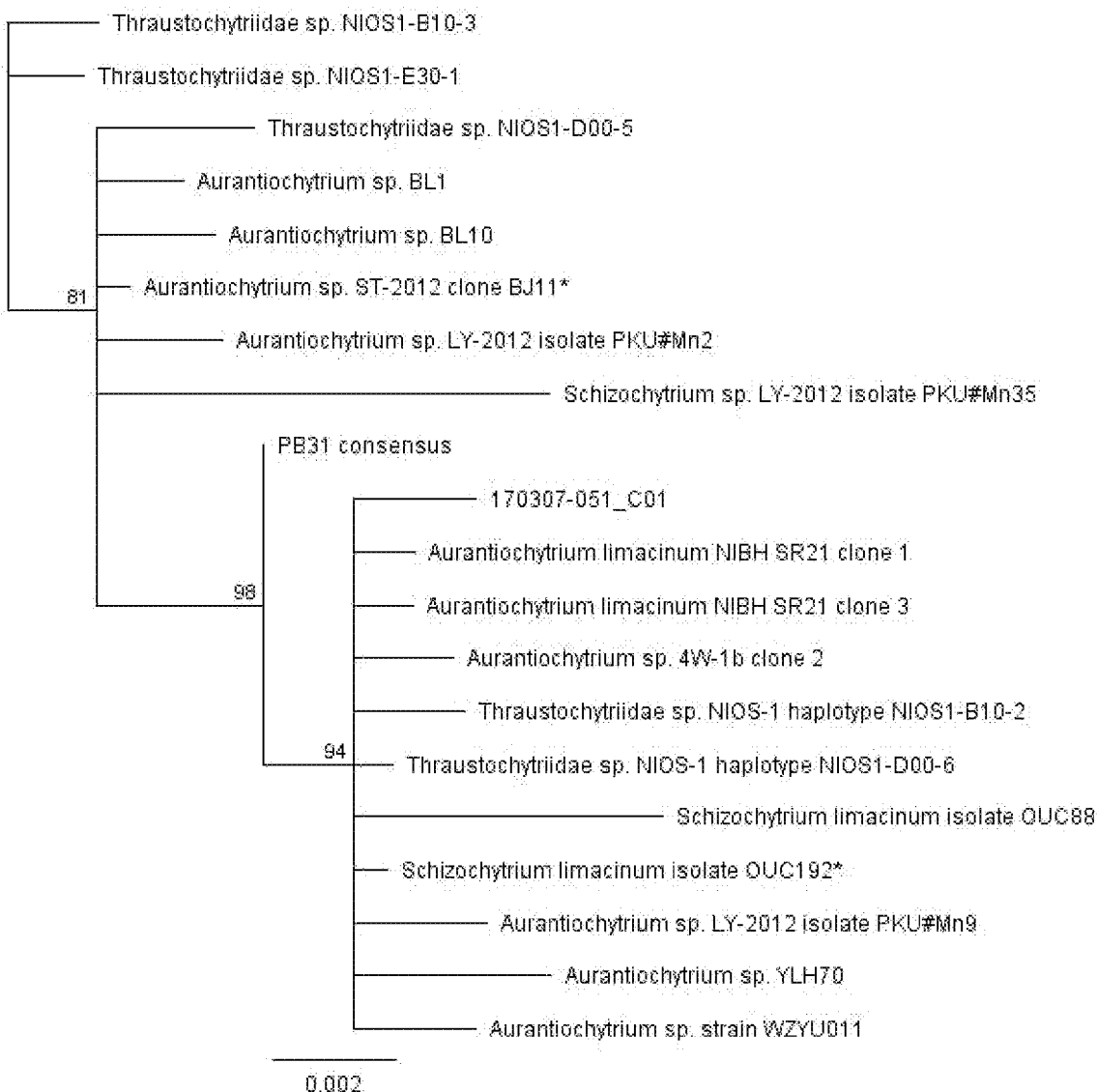

【FIG. 3】
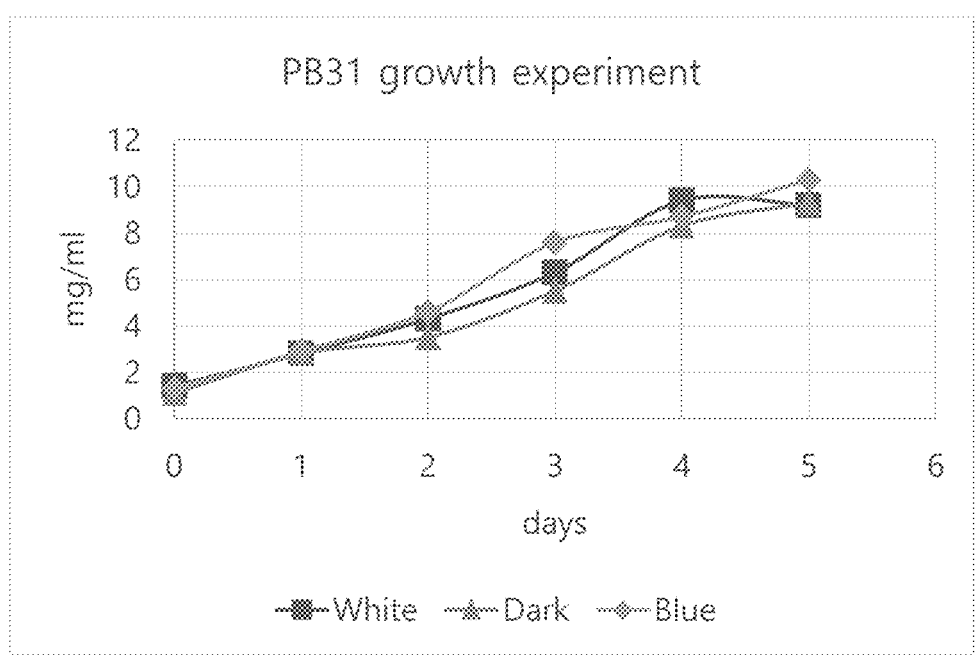
【FIG. 4】
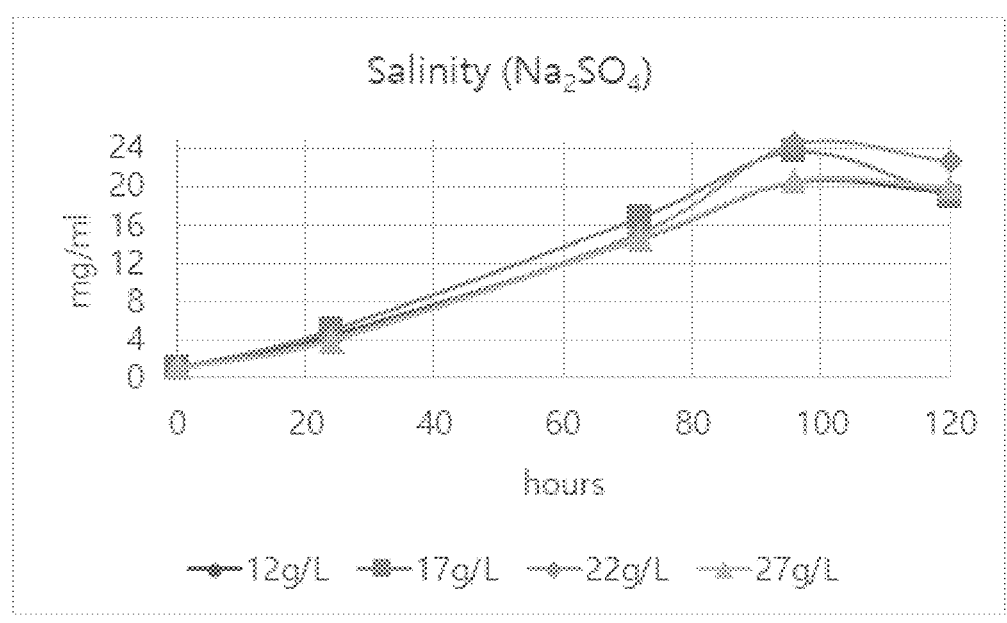

【FIG. 5】
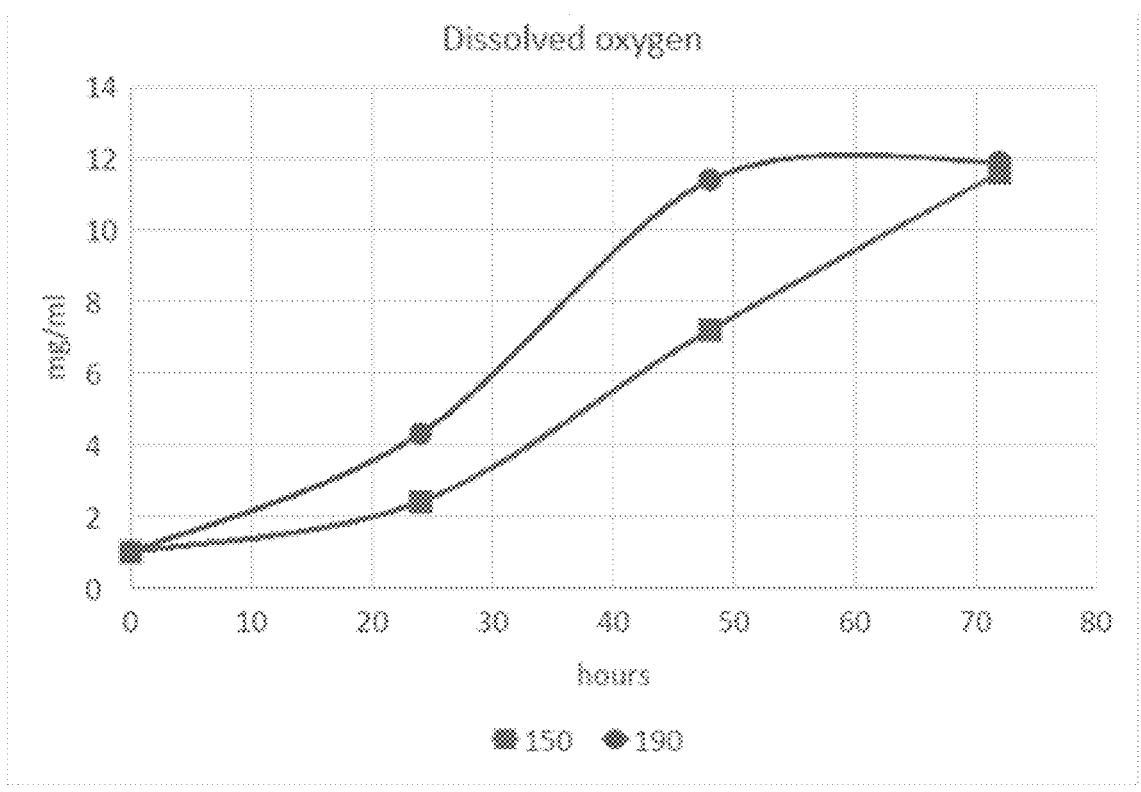
【FIG. 6】
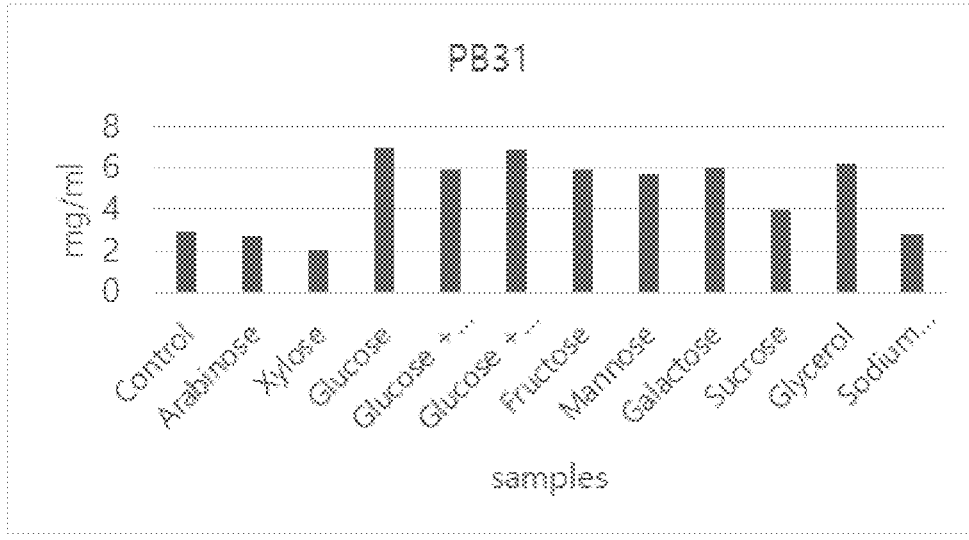

【FIG. 7】
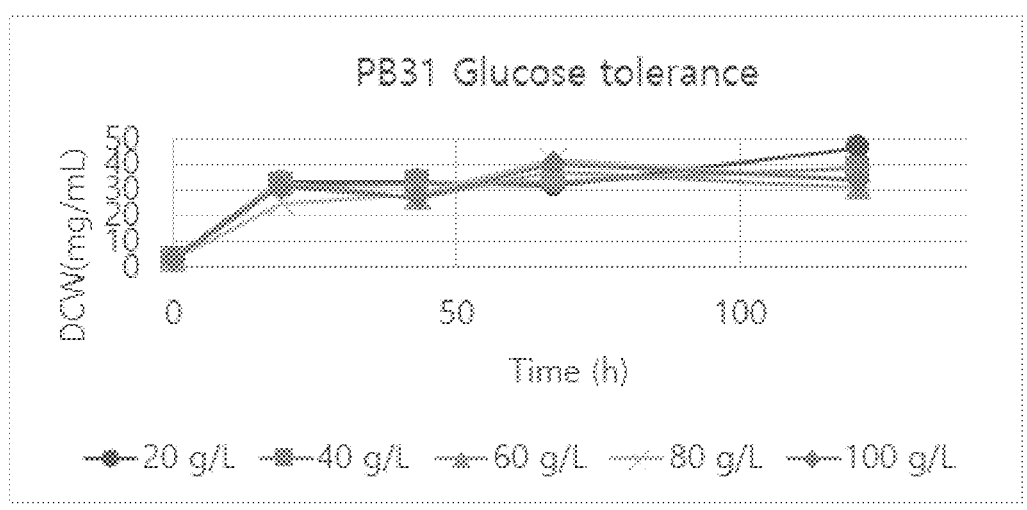
【FIG. 8】
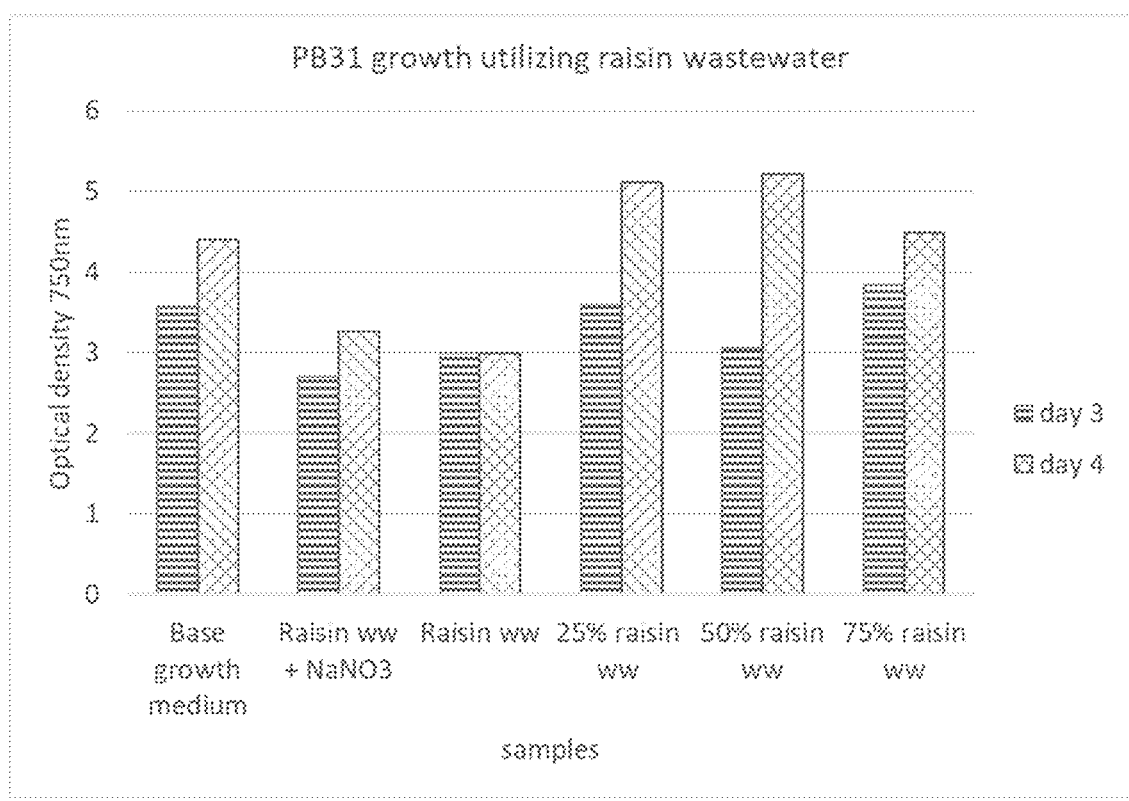

【FIG. 9】 ggatccCTTCTTTCTTTCAGCCTTTGCTGGACTCCCTCGCACGCCTCCTTCTTCCCCAGCCAT
CCATCAGCGGGGCACTCCACCCGCGCTTCAACGCTCGCTCGAGTGCGTGCTTATTTGCCTTC
AACGCGGCGCGGCGGTTAATATAGTCCCAGCACTCCTTAAGGGGGGCATCGCAGGGATTA
TCTTTTCAAAAACCTGTCACGGAGTTACATCTTCCCTCGCATCAAAGTGTTCCCGGCCGCGTC
GCACATCTCAGTTTTATAACCTACACCCCTGGTGGGGTAGGGGCGAATTCTATGTACACAG
CACCTCAGAACTTGCGCGCGTTCCGCGACAAATGAGGGGTGTGGCGGCGCATTCGGCCGC
ATCGCCACATTCAGATATCTAACATACCCCCCCTTCGCGATGAGTGGCAGGCGAGGCGGAT
TCGCTCGCGAGAGGCGAGGTGCCACAGCAGACCAGTAACGAGGAGCCAAGGTAGGTGAC
CACCGACGACTACGACCACGACCACGACCACGACCACAGCCACGGCGGCTGCAGCCACG
GGACGCCTCGCATGGCAGCGCAGCAGCATCAGCAACGACAGCTGCAAGGAGCGCAGGGC
CGATCTGGACGCGCCGGAGCCGCACGACCAATGCCGACGCAACGCTGATTCTTCTGGATT
CCCTCTATACATGCATATATATGCAGAGAAGCGGATGAAATGGCCTGCGAATAAATGAAT
GGCTTGGAGTTTGCTTGCCGTATGCTCGAAAGTGCGTGTGTAGACACAGGCACGACCGAGA
GGACAACAGTCTGTGCTTACCTCACCAGCACATTCTTGCAACGCCATACGAAGCACGCGAA
ATTTTGTGGCTCAGAGCAAAAGGCATTCGTGGTACGGGAACGTGGGGAACGCTATCAATTT
GGAATTCAAAATGAGTGAACCAGACAACTAACTGTGACTTGAACTGTTGCTCCACGCATCAA
AACCAAACCCTTAACAGAAGTAGACCAGTTCAAAGCTACTAGCACCAAACAAAA*TGattgaacaa*
*gatggattgcacgcaggttctccggccgcttgggtggagaggctattcggctatgactgggcacaacagacaatcggctgctctgatgc*
*cgccgtgttccggctgtcagcgcaggggcgcccggttcttttgtcaagaccgacctgtccggtgccctgaatgaactgcaggacgagg*
*cagcgcggctatcgtggctggccacgacgggcgttccttgcgcagctgtgctcgacgttgtcactgaagcgggaagggactggctgct*
*attgggcgaagtgccggggcaggatcatcctgtcatctcaccttgctcctgccgagaaagtatccatcatgcgtgatgcaatgcggcggct*
*gcatacgcttgatccggctaccgtcccattcgaccaccaagcgaaacatcgcatcgagcgagcacgtactcggatggaagccggtctt*
*gtcgatcaggatgatctggacgaagagcatcaggggctcgcgccagccgaactgttcgccaggctcaaggcgcgcatgcccgacg*
*gcgaggatctcgtcgtgacccatggcgatgcctgcttgccgaatatcatggtggaaaatggccgcttttctggattcatcgactgtggccg*
*gctgggtgtggcggaccgctatcaggacatagcgttggctaccgtgatattgctgaagagcttggcggcgaatgggctgacgctcct*
*cgtgctttacggtatcgccgctcccgattcgcagcgcatcgccttctatcgccttcttgacgagttcttc*TGAAGATCCGCGCTGG
CTACGCACCAGTCCTCGATTGCCACACCGCCCACATTGCCTGCAAGTTCGCCGAGATCCAG
AACAAGATGGACCGTCGTTCCGGTAAGATCCTTGAGGATGCCCCCAAGTTCATCAAGTCCG
GTGACTCCGCCATGGTCAAGATGATCCCCTCCAAGAAGATGTGCGTTGAGTCCTTCACTGA
GTACCCTCCCCTCGGCCGCTTCGCCGTCCGTGACATGCGTGTCACCGTCGCCGTCGGTGT
CATCAAGGAGGTTGAGAAGGGTGACAAGTAAGTGGTTTGACCTCTTATACTTGATCGAAATA
CTACCTACACTTAACCTTTTTTGCGATTTTATCGTGATTAGTTTGCTTTTTCTTGATTCGTTTC
TATTCTTCCAAAGTTGTGTCGACCCGTCGTATTGTGTTGATTATTCCGCAGGCTGGTTGTAT
CTTGTTATCATATTTTTTTCTTGAAAGTCGTTGAAGTCCGCGGTTCTGCCATTTCCTATGGAGG
TGTTTTGTTATGAAGCTAGGATGTAAGTTTCTTGTTTTGTAGTGTTGTCTTGAAAGAGTTAAG
CTTTTAATTTTAGTATGTTTTAGAGATTGATTCAGCATGGATATTCAGGATAGTGTACTTGATG
GTACAATCGTTGTTAATGGTTCGTCGTCTGTTTTTATAATTTAAAGATTTGACATGTCGGAAA
AGGTCACAACAGATGGAGTCCCCCGATTTTGGAGTGGTTGTTGGAGATTTTGGCATTTTTAG
ATGATTTTTTTTTCTGTGTTCTGCTACGCTGTTGCATACACTTGCTTATGTTTAAGATTGATGC
TTGTAAGATACCAGGGTTGATTGAGATAGCTCTAGATGTTTATTTATGGTATTAGGTATTGTG
AACTACGAAATCATTGATGTTTGAAAATATACTAACGTTTCTACTGTAAAACATGATGGTTATA
GGTCTCTAAGAAAATAGGTTTATGGTATATTAAGCGATGGATAAAATTTGTTTAAGAGGAAAG
TATTCGATATCGCAACTGTGTCGATCAACGATGGGCAAAGAATCTATTCGCTAAATCAAAAA
CCTATCCTGTCTGTCGTTGGCGTGCGACCAAGAAGCACGGGTTCGGCAGCAGGTACTGTTT
GGAGCTCGAGAAGAGCTTAGTAAACGCTGAGGTGCCTCCATCGTGGGAGCCATCAGAGAG
ATTTCTGCTGCTTCACTTTCGTTGGAAAGTGGAGTGAACCATCTGTTCGATACCTGGACCAC
AACGTGAGTTGGGAAACAGTCTTGCTTTGAGGCAGTTTGCAGCCGCTTAGATTTTTTAGATT
TTGGTAAAGTTCGAAGAGGACATTTGACTGGTTTTGTCTCATAGCTTGTTTTCTTTACAGAAC
AACACTACTCATTGATTTAAAGCGGTGCGAACGAATTTCAATTGATTCGCTGCATTCTATTTC
ATATCAGTTAAAATGGGTAGCGACAATAACCGATCGCGGGTAGAAAACCTGCCAAggatcc

【FIG. 10】

*ATGcttcttcaagcatttctttttcttcttgctggttttgctgctaagatttctgcttctatgacaaacgagacatctgatc
gccctcttgttcattttacacctaacaagggttggatgaacgatcctaacggtctttggtacgatgagaaggatgct
aagtggcatctttactttcaatacaaccctaacgatacagtttggggtacacctctttttggggtcatgctacatctg
atgatcttacaaactgggaggatcaacctattgctattgctcctaagcgcaacgattctggtgctttttctggttctatg
gttgttgattacaacaacacatctggtttttttaacgatacaattgatcctcgccaacgctgcgttgctatttggacata
caacacacctgagtctgaggagcaatacatttcttactctcttgatggtggttacacatttactgagtaccaaaaga
accctgttcttgctgctaactctacacaatttcgcgatcctaaggttttttggtacgagccttctcaaaagtggattatg
acagctgctaagtctcaagattacaagattgagattactcttcagatgatcttaagtcttggaagctcgagtctgct
tttgctaacgagggtttttcttggttaccaatacgagtgccctggtcttattgaggttcctactgagcaagatccttctaa
gtcttactgggttatgtttatttctattaaccctggtgctcctgctggtggctctttttaaccaatactttgttggttcttttaac
ggtacacattttgaggcttttgataaccaatctcgcgttgttgattttggtaaggattactacgctcttcaaacatttttta
acacagatcctacatacggttctgctcttggtattgcttgggcttctaactgggagtactctgctctttgttcctacaaac
ccttggcgctcttctatgtctcttgttcgcaagtttctcttaacacagagtaccaagctaaccctgagacagagctta
ttaaccttaaggctgagcctattcttaacatttctaacgctggtccttggtctcgctttgctacaaacacaacacttac
aaaggctaactcttacaacgttgatctttctaactctacaggtacacttgagtttgagcttgtttacgctgttaacaca
acacaaacaatttctaagtctgttttttgctgatctttctctttggtttaagggtcttgaagatcctgaggagtaccttcgc
atgggttttgaggtttctgcttcttcttttttcttgatcgcggtaactctaaggttaagtttgttaaggagaacccttacttt
acaaaccgcatgtctgttaacaaccaaccttttaagtctgagaacgatctttcttactacaaggtttacggtcttcttg
atcaaaacattcttgagctttactttaacgatggtgatgttgtttctacaaacacatacttatgactacaggtaacgc
tcttggttctgttaacatgacaacaggtgttgataacctttttacattgataagtttcaagttcgcgaggttaagTAA*

【FIG. 11】

*ATGgctaagcttacatctgctgttcctgttcttacagctcgcgatgttgctggtgctgttgagtttggacagatcgcc
ttggttttctcgcgattttgttgaggatgatttgctggtgttgttcgcgatgatgttacactttttatttctgctgttcaagat
caagttgttcctgataacacacttgcttgggtttgggttcgcggtcttgatgagctttacgctgagtggtctgaggttgt
ttctacaaactttcgcgatgcttctggtcctgctatgacagagattggtgagcaaccttggggtcgcgagtttgctctt
cgcgatcctgctggtaactgcgttcattttgttgctgaggagcaagatTAA*

【FIG. 12A】 ggatccCACCTGTTTCTACCAGGAACCTGACCCCTTAGGTTTTGGGGTAGGC
ATGCGCTAGTGGTGTTTGTTAGTTGGGGATTGTTTCGAAAAGAGGTGCTTT
CAAATGATATGTATATATATAATATATTCATTCATGTATGTTTTGAAATACCTA
GCACTTTTGAAAAGCGAGTTGTTAGTGAATCGTCTATTGTTGGCAGAAGGA
CAAGGCCTGAGCAGAAAGAAGAAGGCAGCAAATCCAAATCGAACGGGATTT
GACGGAAAGGAGTCGCGCAGAGCTCGCACTCCGACGTTGCTTTTCAAGGA
AACGGCTGTACGCAGCACAAGACACAAGTCCAGACAGCCAGACGCAGCAG
ACAGGACTCGCTCAGCCTCCCAGAATTAGAGGCAGTCGCACCTTGTTTCGA
TCCTCCCTCCCTCCTCTCCCAGGGAACACATACCTCGTCGGTGTGTTT
CTCTGTATCATCTCTTTCTCCTGACCAGCTTCTACTTCTACTTCTGTAGAA
AGCAGCAGCACTAGTGCAATCTTCAAAAGCACAGCTCAGCTAGCGACAAGA
AGAAGAAGAAGATCTCTTCTTGATCCTGCTGCCTGCTGTGGAACGACCGGC
ACATATACATAACTTTTCATTCGTTCCTTTGCACAACTTGCCGGAATTTGC
GGACTTCACTGACCGCGACAACCAAGTCTCGTGCCGTAAATCTTTCTACGC
AGCTCCTCCTTCTTCATTGCAACAGGCGGCGGCTCTCCTCTGATCCCCCCA
GTCCTTGTCGTTGTACAAAGAAACATCAGAAGAAGAGCATTCTACAGAAGA
AGAAAAGAAGATCTTCATTGTTGAAAAACCATAACC*ATGattgaacaagatggattgc
acgcaggttctccggccgcttgggtggagaggctattcggctatgactgggcacaacagacaatcggctgctct
gatgccgccgtgttccggctgtcagcgcaggggcgcccggttcttttgtcaagaccgacctgtccggtgccctg
aatgaactgcaggacgaggcagcgcggctatcgtggctggccacgacgggcgttccttgcgcagctgtgctcg
acgttgtcactgaagcgggaagggactggctgctattgggcgaagtgccggggcaggatctcctgtcatctcac
cttgctcctgccgagaaagtatccatcatggctgatgcaatgcggcggctgcatacgcttgatccggctacctgc
ccattcgaccaccaagcgaaacatcgcatcgagcgagcacgtactcggatggaagccggtcttgtcgatcag
gatgatctggacgaagagcatcaggggctcgcgccagccgaactgttcgccaggctcaaggcgcgcatgcc
cgacggcgaggatctcgtcgtgacccatggcgatgcctgcttgccgaatatcatggtggaaaatggccgcttttc
tggattcatcgactgtggccggctgggtgtggcggaccgctatcaggacatagcgttggctacccgtgatattgct
gaagagcttggcggcgaatgggctgaccgcttcctcgtgctttacggtatcgccgctcccgattcgcagcgcatc
gccttctatcgccttcttgacgagttcttcTGAAGATCCGCGCTGGCTACGCACCAGTCCTC
GATTGCCACACCGCCCACATTGCCTGCAAGTTCGCCGAGATCCAGAACAAG
ATGGACCGTCGTTCCGGTAAGATCCTTGAGGATGCCCCCAAGTTCATCAAG
TCCGGTGACTCCGCCATGGTCAAGATGATCCCCTCCAAGAAGATGTGCGTT
GAGTCCTTCACTGAGTACCCTCCCCTCGGCCGCTTCGCCGTCCGTGACAT
GCGTGTCACCGTCGCCGTCGGTGTCATCAAGGAGGTTGAGAAGGGTGACA
AGTAAGTGGTTTGACCTCTTATACTTGATCGAAATACTACCTACACTTAACCT
TTTTTGCGATTTTATCGTGATTAGTTTGCTTTTTCTTGATTCGTTTCTATTCTT
CCAAAGTTGTGTCGACCCGTCGTATTGTGTTGATTATTCCGCAGGCTGGTT
GTATCTTGTTATCATATTTTTTCTTGAAAGTCGTTGAAGTCCGCGGTTCTGC
CATTTCCTATGGAGGTGTTTTGTTATGAAGCTAGGATGTAAGTTTCTTGTTTT
GTAGTGTTGTCTTGAAAGAGTTAAGCTTTTAATTTTAGTATGTTTTAGAGATT
GATTCAGCATGGATATTCAGGATAGTGTACTTGATGGTACAATCGTTGTTAA
TGGTTCGTCGTCTGTTTTTATAATTTAAAGATTTGACATGTCGGAAAAGGTC
ACAACAGATGGAGTCCCCGATTTTGGAGTGGTTGTTGGAGATTTTGGCAT
TTTTAGATGATTTTTTTTTCTGTGTTCTGCTACGCTGTTGCATACACTTGCTT
ATGTTTAAGATTGATGCTTGTAAGATACCAGGGTTGATTGAGATAGCTCTAG
ATGTTTATTTATGGTATTAGGTATTGTGAACTACGAAATCATTGATGTTTGAA

【FIG. 12B】

```
AATATACTAACGTTTCTACTGTAAAACATGATGGTTATAGGTCTCTAAGAAAA
TAGGTTTATGGTATATTAAGCGATGGATAAAATTTGTTTAAGAGGAAAGTATT
CGATATCGCAACTGTGTCGATCAACGATGGGCAAAGAATCTATTCGCTAAAT
CAAAAACCTATCCTGTCTGTCGTTGGCGTGCGACCAAGAAGCACGGGTTCG
GCAGCAGGTACTGTTTGGAGCTCGAGAAGAGCTTAGTAAACGCTGAGGTG
CCTCCATCGTGGGAGCCATCAGAGAGATTTCTGCTGCTTCACTTTCGTTGG
AAAGTGGAGTGAACCATCTGTTCGATACCTGGACCACAACGTGAGTTGGGA
AACAGTCTTGCTTTGAGGCAGTTTGCAGCCGCTTAGATTTTTTAGATTTTGG
TAAAGTTCGAAGAGGACATTTGACTGGTTTTGTCTCATAGCTTGTTTTCTTTA
CAGAACAACACTACTCATTGATTTAAAGCGGTGCGAACGAATTTCAATTGAT
TCGCTGCATTCTATTTCATATCAGTTAAAATGGGTAGCGACAATAACCGATC
GCGGGTAGAAAACCTGCCAATTCAGACAAGTCCGTGCCCAGCTTTGACCTC
CTTCGCTATGCCCCGGTGTCCTTCCCGCTCATTTTCATGACCCAGATGGCA
AACTACATGCGTGTTCTCGAGCTCCTCGGAACCTCGCATGAAAAGGTTGCC
CAGCAGGGTTGGTTCAAGGGCGCTCTCGGCCACAGCCAGGGCGTTGTGG
CTGCTGCCGTCACTGCTGCCGCATCCACCGATCGCGAGCTTCGCAACCTC
TCCGTCGCAGGCCTTGAGTTCATGTCCCAAATTGGTCTTGGCGCCCAGAAG
AGCATGAACTTCGAGCTCTCACGCCGCTCCGCAGGACCCGAGTCCCCAT
GCTGTCCGTGCAAGGCATGAGCGAGGCTACCCTTCTCAAGGCCTTCAAGG
AGGCCACCAAGCTTGCCGTACAAAAGAGACCATGATGGCCAAGTTCTCCA
CATCCTCCAAGGACGACAAGGCTGCCCGAATGCTTCGCAGCGTCTTGGT
ATTGCCCTGTGCAACGGCACAGACGACTATGTGGTCTGTGGCGAGCCCAA
GGACCTCCGCATGCTGCGCAAGGTCATTGTTTCCATGAGCGCCGAGGTCG
GTAAGGAGGCTCAGGCGCGTGTACCCTTTTCCAAGCGCAAGCCCGTAACG
CAGACGACATTTCTTCGCATGACCGCACCCTTTCACAGTGCTCTTAACGCA
GAGGCATTTGAGCAGGTCGCCGCCTGGGCAGCCAGCTCAGCCTTTGGTCA
GGAACTTGCGCAAAGGACTCTTCGCATCCCGGTCTGGGACACTGAGAAGG
GCGCAGACTTGCGAAAGATggatcc
```

【FIG. 13】 gcggccgcACAAACAAAACAAAGCAGGAAAGAAAGAAACAAACAAATATACAAACAAAGAAAG
AAAGAAGTGGTGGGAACTAGGGAAATCAATGTGTTTGCTTCTTTCGCACCTTTGCTTTTCTT
GCTTTTCTTGGTTCTCAAGTAAGCGTTTATCGCGCCCTCAGAAAACAAAATAAAATGATCTAA
CATAACATGAATTTATATTTATTTTATTTGTTTATTAAATAAATGTTTTTTGTAAACCAGAATTT
CACTCTACTTTTGCAACACTGAGAGAGTGCCATCTGCATAATAAGTGGCAGTGTTTTTTTGTT
TATTTTCAAATTAATTATACTTGAACTGCTAGGTCAAGAGGCCGCAGCGGCCTGATGAGATA
AGGACAGAGTAGGCAAGGATGGCAGAAGATCGCGAAAAAAGCGGGAAAGGCAAACGAGCA
GGCCCGAAGGTGAGGTGGAGCTGCTTGTCAAGGTCGCGAGGTTTGTTTGACAGTTATAACA
GCAAGAACTAAGGCAATTTCAAGAATGAAGAGCACTCGAATAAACCGATGAAGCAAAGTGT
GTACATACAAACATACATACGTACAGATGAAAGAACAGATTTTCAATAAAAATGACTTTTTA
GTTTAAACAATGTTTCTGTTTGTTGTTCGCTTTTCATTAATTTGTTGCAAATTATTTTGTTTTT
GTTTTTGTTTTTGTTTTTGAAAATCATAAAAGAGATGCTGCCGCAGACGTCTGCGCGTCTCAT
AGTTGATTGGGTAATCGTTTTGTTGAGTTTTGAAAATGTAAACTTCACTTAGTTGCTCATTTAT
CCTCATTCGTTTGCCCATTTGTTCTCTGTTTGAAGCAGAGTTTTGACTTCTCGCATTCGTGGA
ATCCACCCCTTGCTTGCTTTGCTTGCTTGCTTGCCTGCTTGCTTTGCTTGCTTGCTTGACCA
GCGTGCGCGCTTTTGCCAGCCTAGCCTTCGAGACCTCTTGAAGACCCTTTGGAGCGTCTAG
TTCGAGGTTCTTTCTATTTGCTTCAAGAGAGACAAAATAACAAAGAAAAAGAGAGAAAAAACA
AGCAAAGAAAGAAACAAGGAAACAAACCACAAAGCACGCATCGTGCATCCAAACTTTCATCC
CCCCACTCTCTCTCTCTCTCTCTCTCTCTCTCCTTCCTCGGAAAAGGAGTGAGACAAAGGCA
GACAGCCTCTAGCTTGGCAGCCTCGCAGCTCGTGCGGCGCCAGTTCCTACAGCTTCGCGC
TGTCCAAACGCCAGTCCATCGCAGCTTCGGCTAGCTAGTTGGCTGATTGATTGATTGATTGA
TTGATTGATAGCCTTTATTACGGCGTTGATTAACTGATTGATTATTTGATTGCTCTGGCATCC
CTGTAATCACTTGCTCAAGGTAATCAATCACATCATTTATACATCTCCTCCAAAGCAAACCAT
CTACACGACCGCTTTTTGATCGATCTAAAAGTGCCGGTCAGGTGACACGCAAGCTCTTTTTT
TGTTTACAGTAAGCAGCAACAAGAAAGCAAAAAGATGattgaacaagatggattgcacgcaggttctccggcc
gcttgggtggagaggctattcggctatgactgggcacaacagacaatcggctgctctgatgccgccgtgttccggctgtcagcgcaggg
gcgcccggttctttttgtcaagaccgacctgtccggtgccctgaatgaactgcaggacgaggcagcgcggctatcgtggctggccacga
cgggcgttccttgcgcagctgtgctcgacgttgtcactgaagcgggaagggactggctgctattgggcgaagtgccggggcaggatctc
ctgtcatctcaccttgctcctgccgagaaagtatccatcatggctgatgcaatgcggcggctgcatacgcttgatccggctacctgcccatt
cgaccaccaagcgaaacatcgcatcgagcgagcacgtactcggatggaagccggtcttgtcgatcaggatgatctggacgaagagc
atcaggggctcgcgccagccgaactgttcgccaggctcaaggcgcgcatgcccgacggcgaggatctcgtcgtgacccatggcgat
gcctgcttgccgaatatcatggtggaaaatggccgcttttctggattcatcgactgtggccggctgggtgtggcggaccgctatcaggaca
tagcgttggctacccgtgatattgctgaagagcttggcggcgaatgggctgaccgcttcctcgtgctttacggtatcgccgctcccgattcg
cagcgcatcgccttctatcgccttcttgacgagttcttcTGAAGGCCAATAGGACGCCCAAGCCGAACAGTAGCA
ACACCTGGAAGTCCCTGCAGCCACCCCTTCCTTCATCTGGGAGGACTAGCCACACGACCCT
AGATATAATGGCCTCTCGCAAGAATGTGAGCGCTGCTCACGAAATGCACGACGAGAAGCGC
ATTGCCGTGGTGGGCATGGCCGTGCAATACGCGGGCTGCAAAGACAAGGAAGAGTTCTGG
AAAGTAGTCATGGGCGGTGAGGCTGCATGGACTAAGATTAGCGATAAACGCCTCGGATCCA
ACAAGCGAGCCGAGCACCTCAAAGCAGAGCGTAGCAAATTTGCAGATACCTTTTGCAACGA
GAACTACGGCTGCGTCGATGACTCCGTCGATAACGAACACGAGCTTCTCCTTAAGCTCTCC
AAGAAGGCTCTGTCCGAGACATCGGTCTCCGACTCTACAAGGTGCGGTATTGTGAGCGGAT
GCCTGTCCTTTCCCATGGACAACCTCCAGGGCGAACTCCTCAATGTGTACCAAAACCACGT
CGAAAAGAAACTCGGCGCTCGCGTCTTCAAGGATGCCTCCAAGTGGTCCGAGCGTGAGCA
GTCGCAGAACCCCGAGGCTGGTGACCGCCGCATCTTTATGGACCCGGCATCCTTCGTAGC
AGAAGAGCTCAACCTCGGTCCTCTTCACTACTCTGTCGATGCTGCCTGTGCCACCGCCCTT
TACGTCCTTCGCCTCGCCCAGGACCACCTCGTTTCTGGTGCTGCTGATGTCATGCTCGCTG
GTGCAACTTGCTTCCCGGAGCCCTTTCTCACCCTCTCCGGATTCTCCACTTCCAGGCCATG
CCTGTATCGGGAGACGGCATCTCGTACCCGCTTCACAAGGACAGTCAGGGTCTCACCCCTG
GTGAAGGTGGTGCCATTATGGTTCTCAAGCGCCTTGACGACGCTATTCGCGATGGAGACCA
CATTTACGGTACTCTGCTCGGTGCTACCATCAGCAATGCTGGCTGTGGTCTTCCCCTCAAG
CCGCACTTGCCCAGCGAGAAGTCCTGCCTCATTGATACCTAgcggccgc

【FIG. 14】 gcggccgcCAAATCAATTAGCAGTCTATCGTGATATTAGTTAGTAACTAACAAACTAACAAACA
GATAAACAGACAAACAGACAAACAAACAAAACAAACAAAACAAACAAAACAAACAAAACAAA
GCAAGAAAGAAAGAAACAAACAAATATACAAACAAAGAAAGAAAGAAGTGGTGGGAACTAG
GGAAATCAATGTGTTTGCTTCTTTCGCACCTTTGCTTTTCTTGCTTTTCTTGGTTCTCAAGTAA
GCGTTTATCGCGCCCTCAGAAAACAAAATAAAATGATCTAACATAACATGAATTTATATTTATT
TTATTTGTTTATTAAATAAATGTTTTTTTGTAAACCAGAATTTCACTCTACTTTTGCAACACTGA
GAGAGTGCCATCTGCATAATAAGTGGCAGTGTTTTTTTGTTTATTTTCAAATTAATTATACTTG
AACTGCTAGGTCAAGAGGCCGCAGCAGCCTGATGAGATAAGGACAGAGTAGGCAAGGATG
GCAGAAGATCGCGAAAAAAGCGAGAAAGGCAAACGAGCAGGCCCGAAGGTGAGGTGGAG
CTGCTTGTCAAGGTCGCGAGGTTTGTTTGACAGTTATAACAGCAAGAACTAAGGCAATTTCA
AGAATGAAGAGCACTCGAATAAACCGATGAAGCAAAGTGTGTACATACAAACATACATACGT
ACAGATGAAAAGAACAGATTTTCAATAAAAATGACTTTTTAGTTTAAACAATGTTTCTGTTTGT
TGTTTCGCTTTTCATTAATTTGTTGCAAATTATTTTGTTTTTGTTTTTGTTTTTGTTTTTGAAAAT
CATAAAAGAGATGCTGCCGCAGACGTCTGCGCGTCTCATAGTTGATTGGGTAATCGTTTTGT
TGAGTTTTGAAAATGTAAACTTCACTTAGTTGCTCATTTATCCTCATTCGTTTGCCCATTTGTT
CTCTGTTTGAAGCAGAGTTTTGACTTCTCGCATTCGTGGAATCCACCCCTTGCTTGCTTTGC
TTGCTTGCTTGCCTGCTTGCTTTGCTTGCTTGCTTGACCAGCGTGGCGCGCTTTTGCCAGCCT
AGCCTTCGAGACCTCTTGAAGACCCTTTGGAGCGTCTAGTTCGAGGTTCTTTCTATTTGCTT
CAAGAGAGACAAAATAACAAAGAAAAAGAGAGAAAAAACAAGCAAAGAAAGAAACAAGGAAA
CAAACCACAAAGCACGCATCGTGCATCCAAACTTTCATCCCCCCACTCTCTCTCTCTCTCTC
TCTCTCTCCTTCCTCGGAAAAGGAGTGAGACAAAGGCAGACAGCCTCTAGCTTGGCAGCCT
CGCAGCTCGTGCGGCGCCAGTTCCTACAGCTTCGCGCTGTCCAAACGCCAGTCCATCGCA
GCTTCGGCTAGCTAGTTGGCTGATTGATTGATTGATTGATTGATTGATTGATTGATAGCCTTT
ATTACGGCGTTGATTAACTGATTGATTATTTGATTGCTCTGGCATCCCTGTAATCACTTGCTC
AAGGTAATCAATCACATCATTTATACATCTCCTCCAAAGCAAACCATCTACACGACCGCTTTT
TGATCGATCTAAAAGTGCCGGTCAGGTGACACGCAAGCTCTTTTTTTGTTTACAGTAAGCAG
CAACAAGAAAGCAAAAGATGgctaagcttacatctgcttcctgttcttacagctcgcgatgttgctggtgctgttgagttttg
gacagatcgccttggttttctcgcgatttgttgaggatgattttgctggtgttgttcgcgatgatgttacacttttatttctgctgttcaagatcaa
gttgttcctgataacacacttgcttgggtttgggttcgcgggtcttgatgagcttacgctgagtggtctgaggttgtttctacaaactttcgcgatg
cttctggtcctgctatgacagagattggtgagcaaccttggggtcgcgagttgctcttcgcgatcctgctggtaactgcgttcatttgttgctg
aggagcaagatTAAAGGCCAATAGGACGCCCAAGCCGAACAGTAGCAACACCTGGAAGTCCCT
GCAGCCACCCCTTCCTTCATCTGGGAGGACTAGCCACACGACCCTAGATATAATGGCCTCT
CGCAAGAATGTGAGCGCTGCTCACGAAATGCACGACGAGAAGCGCATTGCCGTGGTGGGC
ATGGCCGTGCAATACGCGGGCTGCAAAGACAAGGAAGAGTTCTGGAAAGTAGTCATGGGC
GGTGAGGCTGCATGGACTAAGATTAGCGATAAACGCCTCGGATCCAACAAGCGAGCCGAG
CACCTCAAAGCAGAGCGTAGCAAATTTGCAGATACCTTTTGCAACGAGAACTACGGCTGCG
TCGATGACTCCGTCGATAACGAACACGAGCTTCTCCTTAAGCTCTCCAAGAAGGCTCTCTCC
GAGACATCGGTCTCCGACTCTACAAGGTGCGGTATTGTGAGCGGATGCCTGTCCTTTCCCA
TGGACAACCTCCAGGGCGAACTCCTCAATGTGTACCAAAACCACGTCGAAAAGAAACTCGG
CGCTCGCGTCTTCAAGGATGCCTCCAAGTGGTCCGAGCGTGAGCAGTCGCAGAACCCCGA
GGCTGGTGACCGCCGCATCTTTATGGACCCGGCATCCTTCGTAGCAGAAGAGCTCAACCTC
GGTCCTCTTCACTACTCTGTCGATGCTGCCTGTGCCACCGCCCTTTACGTCCTTCGCCTCG
CCCAGGACCACCTCGTTTCTGGTGCTGCTGATGTCATGCTCGCTGGTGCAACTTGCTTCCC
GGAGCCCTTTCTCACCCTGTCCGGATTCTCCACTTTCCAGGCCATGCCTGTATCGGGAGAC
GGCATCTCGTACCCGCTTCACAAGGACAGTCAGGGTCTCACCCCTGGTGAAGGTGGTGCC
ATTATGGTTCTCAAGCGCCTTGACGACGCTATTCGCGATGGAGACCACATTTACGGTACTCT
GCTCGGTGCTACCATCAGCAATGCTGGCTGTGGTCTTCCCCTCAAGCCGCACTTGCCCAGC
GAGAAGTCCTGCCTCATTGATACCTAgcggccgc

THRAUSTOCHYTRID STRAIN GENETICALLY ENGINEERED FOR THE PRODUCTION OF BIOMATERIALS INCLUDING LONG-CHAIN POLYUNSATURATED FATTY ACIDS

CROSS-REFERENCE TO RELATED APPLICATION

This application claims the benefit of U.S. Provisional Application No. 63/300,101 filed on Jan. 17, 2022, the disclosures of which are herein incorporated by reference in their entirety.

TECHNICAL FIELD

The present invention describes a microorganism having a bio oil-producing ability and a method of producing bio-oil using the microorganism. More specifically, it relates to a method for producing oil having high-value omega-3 and/or 6 oils like ARA, EPA, DPA, and DHA.

BACKGROUND ART

Omega-3 fatty acids such as EPA and DHA have important biological roles in human cognitive, eye, and cardiovascular health. Fish such as salmon, sardines, and mackerels contain high amounts of these fatty acids. The demand for such fatty acids will exceed supply in the near future which combined with the natural source depletion due to climate change, overfishing, and environmental contaminants in the ocean is necessitating the development of alternative, safe, and sustainable sources of such omega-3 oils and long-chain polyunsaturated fatty acids for human consumption. Single-celled marine protists Thraustochytrids, found in coastal brackish waters, have been exploited for the abundance of omega-3 fatty acids, mainly DHA, and some additional amount of omega-6 fatty acids, DPA contributing to high total PUFA contents. *Thraustochytrids* especially strains in genera *Schizoychytrium, Aurantiochytrium*, and *Thraustochytrium* have been cultivated in enclosed fermenters for high omega-3 oil production as an alternative source to fish omega-3 oil for human consumption and cell biomass for animal feed.

BRIEF SUMMARY OF THE INVENTION

Disclosed in this application is a novel thraustochytrid strain named PB31 isolated from coastal waters in Hawaii for commercialization of biomaterials including DHA and its processes for production. The strain produces about 70-80% lipid and DHA comprises 30-50% by weight of that in the commercial scale fermenters.

The processes include cells grown in low-intensity light resulting in a higher growth rate compared to the traditional heterotrophic growing conditions. U.S. Pat. No. 9,932,554 by the applicant of the present application describes the above process with signature culture condition called PSP. This condition combines traditional heterotrophic growth and low irradiance of light (less than 5 μmol photons/m² s¹) as a signal that activates photoreceptors in cells. The light intensity of said process does not activate photosynthesis machinery in the cells and is, therefore, differentiated from mixotrophic growth. The processes also include cultivation, harvesting, drying, extraction, and purification of bioproducts derived from this novel strain of thraustochytrid.

The inventors of the present invention have also developed PB31 as a biotechnology platform to produce various high-value polyunsaturated omega-3 and/or -6 lipids. Efficient nuclear transformation and facile gene targeting by homologous recombination are critical features of this platform. Inventors of the present invention describe seminal experiments to establish a reproducible transformation system in PB31 at various genomic loci. Targeted knockdowns, knockouts, knock-ins, and point mutations in fatty acid or polyketide synthase lipid biosynthetic pathway genes enable the synthesis of tailored polyunsaturated fatty acids in PB31.

Thraustochytrid PB31 can be employed as a general platform for the production of valuable biomolecules including high-value omega-3 and/or 6 oils like ARA EPA, DPA and DHA. Here, the inventors of the present invention demonstrate the utility of the system for the biosynthesis of modified omega-3 and/or 6 fatty acids.

An object of the present invention is to provide microorganism having high polyunsaturated fatty acid productivity, and improving efficiency of a culture process, thereby allowing bio-oil to be prepared economically.

Another object of the present invention is to provide a method of preparing bio-oil using the microorganism.

In order to achieve the above objects, the present invention provides a microorganism, PB31, also designated as *Schizochytrium* sp. PB31 (PTA-123692), also just PTA-123692 herein, having bio-oil producibility.

Further, the present invention provides a method of preparing bio-oil, the method comprising the steps of: (1) culturing the microorganism PB31, and (2) extracting and separating bio-oil containing omega-3 and/or 6 polyunsaturated fatty acids from the cultured microorganism.

ADVANTAGEOUS EFFECTS

The present invention shows that when using microorganism, oil having high-value omega-3 and/or 6 oils like-ARA, EPA, DPA and DHA can be effectively produced.

DESCRIPTION OF THE DRAWING

FIG. 1 shows the morphological features of PB31.

FIG. 2 shows a diagram of Phylogenetic analysis placing PB31 within the lineage that includes *Schizochytrium, Aurantiochytrium*, and Thraustochtriidae.

FIG. 3 is a graph showing biomass production under different growing conditions.

FIG. 4 is a graph showing effect of salinity on PB31 biomass production.

FIG. 5 showing cells grown on a shaker with variable speeds.

FIG. 6 is a graph showing PB31 productivity in various feedstocks.

FIG. 7 is a graph showing the glucose tolerance of PB31

FIG. 8 is a graph showing PB31 growth in wastewater produced when processing raisins.

FIG. 9 shows nucleotide sequence of the transforming DNA contained in plasmid pPB0128.

FIG. 10 shows nucleotide sequence of PB31 codon-optimized *S. cerevisiae* SUC2 gene (ScSUC2) in plasmid pPB0136.

FIG. 11 shows nucleotide sequence of PB31 codon-optimized *S. hindustanus* bleomycin resistant gene in plasmid pPB0240.

FIGS. 12A and 12B show nucleotide sequence of the transforming DNA contained in plasmid pPB0152.

FIG. 13 shows nucleotide sequence of the transforming DNA contained in plasmid pPB0218.

FIG. 14 shows nucleotide sequence of the transforming DNA contained in plasmid pPB0258.

DETAILED DESCRIPTION OF THE INVENTION

Unless otherwise defined herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner like a term "comprising." The transitional terms/phrases (and any grammatical variations thereof) "comprising," "comprises," "comprise," "consisting essentially of," "consists essentially of," "consisting," and "consists of" can be used interchangeably.

The phrases "consisting essentially of" or "consists essentially of" indicate that the claim encompasses embodiments containing the specified materials or steps and those that do not materially affect the basic and novel characteristic(s) of the claim.

The term "about" means within an acceptable error range for the value as determined by one of ordinary skills in the art, which will depend in part on how the value is measured or determined, i.e., the limitations of the measurement system. Where values are described in the application and claims unless otherwise stated the term "about" meaning within an acceptable error range for the particular value should be assumed. In the context of compositions containing amounts of ingredients where the term "about" is used, these compositions contain the stated amount of the ingredient with a variation (error range) of 0-10% around the value (X±10%).

"Fatty acids" shall mean free fatty acids, fatty acid salts, or fatty acyl moieties in a glycerolipid. It will be understood that fatty acyl groups of glycerolipids can be described in terms of the carboxylic acid or anion of a carboxylic acid that is produced when the triglyceride is hydrolyzed or saponified.

"Fixed carbon source" is a molecule(s) containing carbon, typically an organic molecule that is present at ambient temperature and pressure in solid or liquid form in a culture media that can be utilized by a microorganism cultured therein. Accordingly, carbon dioxide is not a fixed carbon source.

The usage of the term "microorganism" in the ensuing patent encompasses, but is not limited to, the following terms: "microalgae," "marine protists," "thraustochytrids," and any other potential taxonomic classification associated with the PB31 microorganism, such as *Schizochytrium, Aurantiochytrium, Thraustochytrium*, and Thraustochtriidae as described herein. All taxonomic classifications used in this patent in reference to the PB31 microorganism are based upon present taxonomic classifications and available phylogenic information but are not intended to be limiting in the event that the standards for the taxonomic classifications used in this patent are revised after the filing date of the present application.

"Microalgae" are eukaryotic microbial organisms that contain a chloroplast or other plastid, and optionally that can perform photosynthesis. Microalgae include obligate photoautotrophs, which cannot metabolize a fixed carbon source as energy, as well as heterotrophs, which can grow by a fixed carbon source. Microalgae include unicellular organisms that separate from sister cells shortly after cell division, such as *Chlamydomonas*, as well as microbes such as, for example, Volvox, which is a simple multicellular photosynthetic microbe of two distinct cell types. Microalgae include cells such as *Chlorella, Dunaliella*, and Prototheca. Microalgae include, other microbial photosynthetic organisms that exhibit cell-cell adhesion, such as *Agmenellum, Anabaena*, and Pyrobotrys. Microalgae also include groups of unicellular microbials characterized by the presence of two flagella, or with immature tripartite hair like flagellum or unicellular or colonial microorganisms that have flagellate stage in their life cycles such as diatoms, dinoflagellates and thraustochytrids.

In connection with a recombinant cell, the term "knockdown" refers to a gene that has been partially suppressed (e.g., by about 1-95%) in terms of the production or activity of a protein encoded by the gene.

An "oleaginous" cell is a cell capable of producing at least 20% lipid by dry cell weight, naturally or through recombinant or classical strain improvement. An "oleaginous microbe" or "oleaginous microorganism" is a microbe, including a microalga that is oleaginous (especially eukaryotic microalgae that store lipid). An oleaginous cell also encompasses a cell that has had some or all its lipid or other content removed, and both live and dead cells.

In connection with a functional oil, a "profile" is the distribution of species or triglycerides or fatty acyl groups within the oil. A "fatty acid profile" is the distribution of fatty acyl groups in the triglycerides of the oil without reference to the attachment to a glycerol backbone. Fatty acid profiles are typically determined by conversion to a fatty acid methyl ester (FAME), followed by gas chromatography (GC) analysis with flame ionization detection (FID). The fatty acid profile can be expressed as one or more percent of fatty acid in the total fatty acid signal determined from the area under the curve for that fatty acid.

The terms "triglyceride", "triacyl glyceride" and "TAG" are used interchangeably as is known in the art.

In the present disclosure, ranges are stated in shorthand, to avoid having to set out at length and describe each value within the range. Any appropriate value within the range can be selected, where appropriate, as the upper value, lower value, or the terminus of the range. For example, a range of 0.1-1.0 represents the terminal values of 0.1 and 1.0, as well as the intermediate values of 0.2, 0.3, 0.4, 0.5, 0.6, 0.7, 0.8, 0.9, and all intermediate ranges encompassed within 0.1-1.0, such as 0.2-0.5, 0.2-0.8, 0.7-1.0, etc. When ranges are used herein, combinations and sub-combinations of ranges (e.g., subranges within the disclosed range), specific embodiments therein are intended to be explicitly included.

In the present invention, in order to develop microorganism as a biotechnology platform having various high-value polyunsaturated omega-3 and/or 6 lipids producibility, the microorganism of Thraustochytrid has been separated from shallow waters in Hawaii.

Therefore, in one aspect, the present invention relates to PB31 having bio-oil producibility.

The microorganism of the present invention, PB31 is the microorganism, classified as a Thraustochytrid and has omega-3 and/or 6 polyunsaturated fatty acid producibility.

The microorganism of the present invention is a microorganism separated from shallow waters in Hawaii, and may have a DNA sequence of a 18S rRNA gene indicated as SEQ ID NO: 1. As a result of a search using NCBI (National Center for Biotechnology Information) BLAST, it was found to be novel microorganism of a *Thraustochytrium* family, and deposited with the American Type Culture Collection (ATCC) (Manassas, VA, USA) as *Schizochytrium* sp. PB31, Accession No. PTA-123692 on Dec. 1, 2016.

The bio-oil produced by PTA-123692, with in-house designation PB31, according to the present invention is characterized in that it may be included in 70 wt % or more of the dry biomass, and the content of polyunsaturated fatty acids contained in the bio-oil may be 30 to 55 wt % based on the weight of total fatty acids (TFA). The polyunsaturated fatty acid may be docosahexaenoic acid (DHA), docosapentaenoic acid (DPA), arachidonic acid (ARA), Eicosapentaenoic acid (EPA), or a mixture thereof, but is preferably docosahexaenoic acid. Preferably, docosahexaenoic acid is characterized in that it is included in 30% or more, preferably 30 to 50 wt % with respect to the total fatty acid content. The bio-oil produced by the PB31 may further include saturated fatty acids such as palmitic acid or other fatty acid components in addition to the polyunsaturated fatty acids.

In addition, as a result of analyzing the morphological characteristics and biochemical characteristics to identify the microorganism of the present invention, PB31 according to the present invention has the characteristics of the genus *Schizochytrium* that are continuously divided into tetrad and octad before cells generate zoospore, and produce irregularly shaped amoeba cells (see FIG. 1).

PB31 provided by the present invention has advantages that PB 31 strains are robust organisms that grow rapidly and perform well under industrial/commercial scale fermentation conditions such as high pressure and high shearing force. PB31 does not produce significant amounts of other by-products (such as polysaccharides) during the cultivation such by-products interfere with optimum cell biomass and oil productivity. Another advantage is that the cell wall of PB31 is robust enough to withstand the high pressure in the large-scale fermenter and pre-treatments or additional steps are not required to break the cell open to extract oil during downstream processing. Another advantage is that the organism can be easily and efficiently transformed that facile gene targeting by homologous recombination is reproducible by transformation at various genomic loci enabling targeted knockdowns, knockouts, knock-ins, and point mutations in fatty acid or polyketide synthase lipid biosynthetic pathway genes, and thus, it can be employed as general industrial biotechnology and metabolic engineering platform for the production of valuable biomolecules including high-value omega-3 and/or 6 oils like ARA, EPA, DPA, and DHA.

In the present invention, the content of polyunsaturated fatty acids such as DHA in the biomass containing the microorganism, PB31, when culturing it and the bio-oil extracted therefrom are high, and cells can be cultured at high concentrations. There is an advantage in that bio-oil containing a high content of polyunsaturated fatty acids can be obtained with high productivity and high yield.

In another aspect of the invention, the present invention provides a method for using PB31 as platform for the production of polyunsaturated fatty acids.

In another aspect of the invention, the present invention provides an industrial biotechnology platform for the production of polyunsaturated fatty acids comprising PB31.

In examples of the present invention, PB31 can be efficiently and reproducibly transformed using a modified lithium acetate (LiAc) transformation method.

Also, homologous recombination occurs in PB31 and can be used as a tool to modulate various enzyme activities by gene knockdowns, knockouts, and knock-ins.

Homologous recombination in PB31 can be used to enhance or suppress a target gene activity by replacing endogenous regulatory elements with up- or down-regulated heterologous regulatory elements.

Specific point mutations can be introduced into endogenous enzymes to affect an alteration in the catalytic activity of target enzymes resulting in an enhanced product profile or even novel products.

An optimum combination of homologous recombination-based gene knockdowns, knockouts, knock-ins, coupled with specific point mutations and/or endogenous regulatory element modulation will yield novel product profiles in PB31.

Yet another aspect of the invention concerns the use of PB31 of the present invention, biomass comprising the same, or a concentrate or dried product of the biomass or the bio-oil isolated from said microorganism in the production of foodstuffs, beverages, nutritional preparations, pharmaceutical preparations, animal feed or cosmetic products.

Specifically, PB31 provided in the present invention, biomass comprising the same, or a concentrate or dried product of the biomass may be used in animal feed (particularly added or mixed for feed and pet food for cattle, pigs, chickens, goats, sheep) or aquatic animal feed without further purification or processing.

Accordingly, in another aspect, the present invention provides a composition for feed comprising a group consisting of PB31, biomass obtained by fermenting PB31, concentrates or the above biomass, and dried products thereof.

On the other hand, as another aspect, the present invention relates to a method for producing biomass using PB31. The method for producing biomass of the present invention is characterized by comprising the steps of culturing and fermenting PB31.

The culture of PB31 in the above production method may use a culture method such as conventional heterotrophic fermentation, a closed photo-bioreactor, or an open pond system.

In a specific aspect, a characteristic of the production method according to the present invention is to cultivate the *Schizochytrium* sp. PB31 (PTA-123692) under conditions of giving a light signal having a light intensity in a specific range in the culture. Preferably, the light intensity means a light amount of very weak light that prevents cultivation in an autotrophic mode or a mixed nutrition mode, specifically 0.1 μmol/m²·s to 5 μmol/m²·s, 0.1 μmol/m²·s to 4 μmol/m²·s, 0.1 μmol/m²·s to 3 μmol/m²·s, 0.5 μmol/m²·s to 5 μmol/m²·s, 0.5 μmol/m²·s to 4 μmol/m²·s, 0.5 μmol/m²·s to 3 μmol/m²·s, 1 μmol/m²·s to 5 μmol/m²·s, 1 μmol/m²·s to 4 μmol/m²·s, 1 μmol/m²·s to 3 μmol/m²·s, or 2 μmol/m²·s to 5 μmol/m²·s. The light signal may be continuous or discontinuous light, may irradiate a full spectrum of light not limited to a specific range of wavelengths, or may give light of a specific wavelength. In the case of culturing by giving a light signal having a light intensity in such a specific range, the microorganism according to the present invention may be cultured in a heterotrophic mode, not in an autotrophic mode or a mixotrophic mode.

In a specific aspect, blue light may be used for the production method. Specifically, the wave length of the light may be 400 to 500 nm, 450 to 500 nm or 450 to 490 nm.

In order to culture PB31, it is preferable to supply a carbon source together with a culture medium. The medium for the culture is not limited as long as it is a medium used for culturing the microorganism and may preferably include seawater. The carbon source may be any carbon source suitable for culturing the microorganism without limitation, it may be preferably monosaccharides such as glucose, fructose, galactose, or mannose, disaccharides such as sucrose, and pentose such as arabinose and xylose, sodium acetate, glycerol, crude glycerol, and the like, but not limited thereto, and glucose is most preferred.

It is preferable to supply the carbon source in a continuous or fed-batch manner so that an appropriate concentration to be maintained. If necessary, a method such as pH-stat or DO-stat may be used, or the concentration of each carbon source may be measured in real time and supplied when necessary.

Examples of such nutritional components include various nitrogen sources, phosphate sources, and other components, which are obvious to those skilled in the art. In addition, as an example of the medium, it is also apparent to those skilled in the art that a complex medium or a defined medium may be used.

Nitrogen sources may include organic nitrogen sources such as yeast extract, corn steep liquor, beef extract, malt extract, peptone, and tryptone, or inorganic sources such as ammonium acetate, ammonium nitrate, ammonium chloride, ammonium sulfate, sodium nitrate, urea, or MSG.

It is preferable to maintain the pH and/or temperature in a preset range while culturing PB31 through the above culture method. As a method for maintaining constant pH and/or temperature during culture, methods well known in the art may be used. For example, a method of using a cooling jacket using cooling water, a method of automatically supplying acid or base using a pH controller, etc. may be used, but are not limited thereto.

Preferably, the concentration of chloride, sodium ion concentration, and potassium ion contained in the culture medium may be 0.6 to 0.8 g/L, 5.0 to 7.0 g/L, and 0.4 to 0.6 g/L, respectively, and the culture may be performed at pH 6 to 8. The acid used to adjust the pH may be preferably sulfuric acid, acetic acid, or a mixed acid thereof.

In a preferred embodiment, the microorganism culture produced by the above production method may be harvested by methods such as centrifugation, flocculation, flotation, and filtration. After harvesting the microorganism product, several drying methods such as spray drying and drum drying may be used to obtain the culture powder.

In another aspect, the present invention provides a method of preparing bio-oil, the method comprising the step of: (1) culturing the PB31 and (2) extracting and separating bio-oil containing omega-3 and/or 6 polyunsaturated fatty acid from the cultured microorganism.

In the present invention, culturing in above step (1) may be carried out in a manner selected from the group consisting of batchwise, fed-batchwise, and continuous culturing, and in above step (2), a cell disruption step may be further included.

The cell disruption may be cell disruption using a supersonic disperser, cell disruption using a pulsed electric field, cell disruption using an enzyme, cell disruption using osmotic pressure, cell disruption using an electron beam, or cell disruption using an organic solvent.

The method of preparing bio-oil of the present invention may further comprise (3) purifying bio-oil containing the omega-3 and/or 6 fatty acid.

In the present invention, the purification may include collecting only an oil phase among an oil phase containing bio-oil and an aqueous phase containing cell pieces, and may be carried out by including one or more steps of removing a solidified oil fraction, bleaching using bleaching clay or activated carbon, filtering, and deodorizing.

In the present invention, the deodorizing step may be carried out by a steam deodorizing process under reduced pressure.

In one embodiment of the present invention, the method of preparing bio-oil containing omega-3 and/or 6 fatty acid using the PB31 may comprise the following steps:

(1) culturing PB31; and (2) collecting the cultured cell biomass, and extracting and separating bio-oil containing omega-3 and/or 6 polyunsaturated fatty acid.

The method may further comprise:

(3) purifying bio-oil containing the separated omega-3 and/or 6 polyunsaturated fatty acid.

Hereinafter, each step will be described in detail.

Culturing of PB31 in above step (1) may proceed in a manner selected from batchwise, fed-batchwise and continuous culturing, and it is preferred to use fed-batchwise or continuous culturing.

In step (1), it is preferred to supply a carbon source for culturing PB31 through the fed-batchwise or continuous culturing. Herein, the carbon source may be used without limitation only if it grows using PB31, and glucose, fructose, sucrose, galactose, glycerol, crude glycerol which is bio-diesel waste, and the like are preferred, but not limited thereto, and glucose is most preferred. It is preferred that the carbon source is supplied in a continuous or fed-batchwise manner so as to maintain proper concentration, and if necessary, a method such as pH-stat or DO-stat may be used, and a method of supplying the carbon source as required by measuring the concentration of each carbon source in real time, and the like may also be used. In addition, a nutrient needed for growth of PB31 may be contained in a medium, and it is apparent to a person skilled in the art that a variety of a nitrogen source, a phosphate source, other components, and the like may be contained, and also a complex medium, a defined medium, or the like may be used. As the nitrogen source, an organic nitrogen source such as yeast extract, corn steep liquor, beef extract, malt extract, peptone, tryptone, and the like, and an inorganic nitrogen source such as acetate, ammonium nitrate, ammonium sulfate, sodium nitrate, urea, and the like may be used.

Particularly, it is preferred to set salt concentration to an appropriate concentration level and proceed with culturing within the range.

In step (1), it is preferred to maintain pH and/or temperature within a predetermined range, during culturing PB31 through fed-batchwise or continuous culturing. As the way to constantly maintain pH and/or temperature during culturing, a well-known method in the art, such as a method of using a cooling jacket with cooling water, a method of using a pH controller to automatically supply acid or base, and the like, may be used, but not limited thereto.

Further, it is preferred that culturing of PB31 through the fed-batchwise or continuous culturing, is carried out under adequate aeration and agitation. An aeration speed and an agitation speed may be appropriately selected by a person skilled in the art according to a process condition. More specifically, since PB31 is aerotropic and has a property of being weak under shear stress by agitation, it is preferred that agitation speed may be selected from 50-300 rpm, preferably 100-300 rpm, and aeration speed may be 0.5-5 vvm, preferably 1-3 vvm.

The content of an omega-3 and/or 6 polyunsaturated fatty acid in the bio-oil produced through culturing of step (1) according to the present invention is 30 wt % or more, preferably 40 wt % or more, most preferably 50 wt % or more, based on total fatty acids.

The step to collect the cultured PB31, and extract and separate bio-oil containing an omega-3 and/or 6 polyunsaturated fatty acid according to step (2), includes a step to disrupt cells, after completing the culturing in step (1). In the step of cell disruption, cell disruption may be induced by methods of cell disruption using a pulsed electric field, cell disruption using an enzyme, cell disruption using an electron beam, and the like, but not limited thereto, and it is apparent to a person skilled in the art that a method of using an organic solvent such as hexane to disrupt cells and extract oil, may be used. Particularly, if the disruption technique is used after cell disruption using osmotic pressure, a cell disruption effect may be enhanced.

As the cell disruption proceeds, phase separation of an oil phase and an aqueous phase containing cell pieces occurs, and only the oil phase is collected at this time, and a final bio-oil product may be obtained through a purification process in step (3).

The purification of bio-oil according to step (3) is carried out by including one or more steps selected from the group consisting of leaving the oil phase at −5-0° C. for 5-20 hours to remove a solidified oil fraction, bleaching the oil fraction using bleaching clay and/or activated carbon, filtering, and deodorizing, and preferably, those steps may be sequentially carried out.

It is preferred to carry out filtering using a filter having a pore size of 0.5-1 μm, and it is also preferred to carry out deodorizing through a steam deodorization process under reduced pressure, but not limited thereto.

The bio-oil produced according to the production method of the present invention is not limited thereto, but may contain about 30 to 55% by weight of polyunsaturated fatty acids, preferably 30% or more by weight of total fatty acids (TFA). Preferably it may contain 30 to 55% by weight of docosahexaenoic acid.

EXAMPLES

Hereinafter, the present invention will be described in detail through the following Examples. These Examples are only for specifically illustrating the present invention, and it is apparent to a person skilled in the art that according to the gist of the present invention, the scope of the present invention is not limited to these Examples.

I. Isolation of the Microorganism

PB31 was isolated from fallen leaves in shallow coastal sea waters. After washing with sterilized seawater, collected leaves were cut into small rectangular pieces and soaked in the same seawater for 24 hours at room temperature. 1 ml of this seawater was transferred to each well in a 12-well plate containing 2 ml sea water, 0.3% yeast extract, 2% glucose, and 300-600 μg/ml penicillin and streptomycin. A couple of pieces of washed leaves were placed on seawater agar plates containing 0.3% yeast extract, 2% glucose, 600 μg/ml penicillin G, and 600 μg/ml streptomycin. After several rounds of dilutions into new 12-well plates and streaking onto new agar plates, the inventors of the present invention were able to get a single axenic cell culture. Each colony isolated from agar plates was transferred to new agar plates and grown to confluence. Once the cells on agar plates were checked for contamination, they were collected and expanded into a 125 ml flask containing 50 ml medium and grown under PSP conditions for four days on an orbital shaker with 150 rpm at room temperature. As cells grew, the culture turned pale yellow, whitish yellow, or vanilla in color. After checking for contamination, some amount of cell culture was transferred into a new flask for maintenance, and the remaining cell cultures were transferred to a clean 50 ml falcon tube and centrifuged at maximum speed for 3 minutes to collect the cell pellet. The pellet was freeze-dried and stored in a −20° C. freezer for further analysis.

II. Identification of the Microorganism

PB31 cells grown for 4 days in a base growth medium containing 2% glucose were harvested by centrifugation. Base growth media consisted of the following in 1 L: 13.5 g Na$_2$SO$_4$, 1.5 g NaCl, 2.57 g MgSO$_4$ 7H$_2$O, 0.3 g CaCl$_2$), 0.75 g NaNO$_3$, 3 g yeast extract, 2.38 g HEPES, 0.027 g NH$_4$Cl, 10 ml stock trace metal solution, 1 ml chelated iron solution, 80 ml 0.1M Phosphate solution (pH7.8) and 1 ml vitamin solution. Stock trace metal solution consisted of the following in 100 ml: 0.1 g Na$_2$EDTA 2H$_2$O, 0.114 g H$_3$BO$_3$, 4.9 mg FeCl$_3$ 6H$_2$O, 1.92 mg MnCl$_2$ 4H$_2$O, 2.2 mg ZnSO$_4$ 7H$_2$O, and 0.48 mg CoCl$_2$ 6H$_2$O. The stock chelated iron solution consisted of the following in 100 ml: 0.5 g Na$_2$EDTA, 10 ml 1M HCl solution, and 0.081 g FeCl$_3$ 6H$_2$O. Sterile stock vitamin solution consisted of the following in 200 ml: 50 mM HEPES (pH7.8) 0.44 g Thiamine-HCl, 0.005 g Biotin, 0.027 g B12 and 0.619 g D-pantothenic acid hemi-calcium. Stock phosphate solution consisted of the following in 1 L: 90.8 ml 1M K$_2$HPO$_4$, and 9.2 ml 1M KH$_2$PO$_4$.

Through microscopic observation and single colony isolation from agar plates, the isolated strain showed the characteristics of the microorganisms belonging to the genus *Thraustochytrids*.

Some zoospores with two flagella were observed, especially at an early stage of the growing period or when no glucose was present in the culture medium. Growing cells actively divided into dyads, tetrads, and octads, and once they went into a stationary growth period, oil droplets accumulated in the cells (FIG. 1). A literature search revealed that "*Schizochytrium* sp. is characterized by the successive bipartition of the cells into tetrads and octads prior to the production of zoospores. *Schizochytrium* also produces "irregularly shaped amoeboid cells" (Mycosphere, Cultural optimization of *Thraustochytrids* for Biomass and Fatty Acid Production, 2011). These observations suggested that the novel PB31 strain described in this patent could be a *Schizochytrium* sp.

To ascertain the genetic identity of our strain, genomic DNA was extracted from PB31 using the CTAB and phenol/chloroform/isoamyl alcohol protocol to amplify partial 18S rRNA gene with primers PB00020 and PB00021 (Honda et. al 1999) using Herculase II fusion DNA polymerase enzyme with dNTPs combo kit (Agilent, USA) followed by Sanger sequencing (Genewiz, USA) of the amplified PCR product. The sequences of the primers used to amplify the 18S rRNA is shown below PB00020 Forward: 5'-AACCTGGTT-GATCCTGCCAGTA-3' (SEQ NO.: 3)

PB00021 Reverse: 5'-CCTTGTTACGACTT-CACCTTCCTCT-3' (SEQ NO.: 4)

The PCR protocol included the following steps 1) 95° C. for 2 minutes,
2) 95° C. for 20 seconds,
3) 50° C. for 20 seconds,
4) 72° C. for 1 min, repeat steps 2 to 4 30 times,
5) 72° C. for 3 minutes and
6) 24° C. for 1 min.

Pair-wise comparison of the 18S ribosomal RNA gene sequences (SEQ 1 and SEQ 2) of the PB31 showed that it was closely related to *Schizochytrium* sp., Thraustochytriidae sp. and *Aurantiochytrium* sp. (Table 1 and FIG. 2).

11

TABLE 1

PB31 18S rRNA sequence comparison to sequences in the
National Center for Biotechnology Information (NCBI) database.
Comparison of 18S rRNA
sequences with PB31 partial 18S rRNA sequence

| Thraustochytrids | percent identity |
|---|---|
| *Schizochytrium* sp. | 88% |
| *Aurantiochytrium* sp. | 86% |
| *Thraustochytriidae* sp. | 79% |
| *Aurantiochytrium acetophilum* | 79% |
| *Aurantiochytrium mangrovei* | 79% |
| *Thraustochytrium aggregatum* | 74% |
| *Schizochytrium* sp. | 98% |
| *Aurantiochytrium* sp. | 98% |
| *Thraustochytriidae* sp. | 98% |
| *Aurantiochytrium acetophilum* | 98% |
| *Aurantiochytrium mangrovel* | 98% |
| *Thraustochytrium aggregatum* | 86% |

III. Growth Experiments and Medium Optimization

Initial inoculum, in 250 ml Erlenmeyer flasks containing 100 ml seawater, 0.3% yeast extract, and 2% glucose, was grown at room temperature in a PSP shaker (a shaker fitted with custom 6-12 white or blue LED light bulbs with light intensity between 0.1 to 1 μmol photons/m² s¹). After 48 hours of growth in the initial flask, 5 ml of the cell culture was transferred to 3 new flasks containing 95 ml base growth medium and 2% glucose. Incubator shakers were prepared as follows: One flask was designated for a dark shaker, one was prepared for shaker fitted with Blue LED light bulbs for PSP experiment condition, and the last one was kept in white light condition with 35 μmol photons/m² s¹. The cell culture was grown for 4-5 days until the all the fed glucose was consumed. 1 ml of cell culture from each flask was collected to measure biomass and glucose consumption every day. Biomass production of PB31 in different conditions is shown in FIG. 3. Growth under PSP conditions resulted in the highest biomass compared to the dark conditions. Based on the lipid data, blue light conditions gave the best productivity as well as higher DHA production (Table 2).

TABLE 2

Fatty acids profile data comparison between PSP
condition and heterotrophic condition.

| | | Fatty Acids (%) | | |
|---|---|---|---|---|
| Run | Condition | C16:0 | C22:6n3 | Total Lipid (%) |
| 1 | Dark | 39 | 42 | 38 |
| | Blue | 41 | 42 | 45 |
| 2 | Dark | 69 | 14 | 33 |
| | Blue | 49 | 34 | 44 |

Unless noted otherwise, the below-described set of experiments was conducted to optimize media for optimum PB31 growth in a PSP shaker at 150 rpm at room temperature.

1. Salinity

The initial inoculum was prepared as described above. 5 ml of initial inoculum was transferred into four 250 ml baffled flasks set up with 95 ml base growth media containing different $Na_2SO_4$ concentrations (12, 17, 22 and 27 g/L), 30 mM MSG and 4% glucose. Cell growth was measured by collecting 1 ml of sample from flasks each day to measure biomass and glucose consumption for 4 to 6 days or until all glucose was consumed. Based on the experiment data, 17 g/L Na2SO4 gave the best growth (FIG. 4).

12

2. Dissolved Oxygen Levels

Two incubator shakers were set up: one shaking at 150 rpm and the other at 190 rpm. Flasks containing 100 ml cell culture were incubated for 3 days. Cell growth in different conditions was measured in the same way as described above. With a faster shaker speed, the inventors of the present invention were able to shorten the growth by nearly 24 hours when compared to that of 150 rpm (FIG. 5).

3. Carbon Sources

Monosaccharides (glucose, fructose, galactose, and mannose), disaccharides (sucrose), and 5-carbon sugars (arabinose and xylose) were used to test the growth of PB31. Other frequently used carbon sources such as sodium acetate and glycerol were also tested in combination with glucose or separately. In 6-well plates, cells were incubated with 1% of various carbon sources. Xylose and arabinose were tested in combination with 1% glucose. Different ratios of glucose and glycerol mixtures were tested in 250 ml flasks with the total working carbon source concentration reaching 2%~4% (w/v) in the cell culture.

Compared to other feedstocks tested, Glucose gave the best productivity in 6 well plate experiments. Glycerol was the next best carbon source used by the cell. Other carbon sources such as galactose, fructose, and mannose also gave good growth. Using a mixture of five-carbon ring sugar (arabinose or xylose) together with glucose did not result in any additive effects when compared with the glucose-only sample (FIG. 6).

PB31 was grown in media containing different concentrations of glucose (20 g/L, 40 g/L, 60 g/L, 80 g/L, and 100 g/L) to determine its glucose tolerance level (FIG. 7). The experiment was conducted for 5 days. While the best biomass productivity was achieved with 20 g/L glucose, higher concentrations of glucose (up to 100 g/L) were tolerated well by PB31 with no significant impact on its growth characteristics suggesting that PB31 can grow efficiently in highly concentrated glucose solutions.

Flask data for PB31 showed higher growth and higher DHA (C22:6n3) productivity with 2 (w/v) % glycerol (16.7 mg/ml, 51.68%) compared to 2 (w/v) % glucose (12.8 mg/ml, 40.33%) (Table 3). We achieved higher biomass, total fatty acids, and DHA productivity when compared to results reported by others (US20090117194; Burja et al data). 4% (w/v) glycerol resulted in a further increase in DHA, TFA, and biomass. A mixture of glucose-glycerol in various ratios also performed better than glucose alone, with improvements seen in TFA, DHA, and biomass being dependent on increasing concentrations of glycerol.

TABLE 3

PB31 fatty acid profile and lipid productivity in shake flasks, grown
on glucose, glycerol, or a mixture of two.

| Samples | Conditions | C16:0 (%) | C22:6n3(%) | Total fatty acids (%) | Biomass (g/L) |
|---|---|---|---|---|---|
| 1 | 2% glucose | 42.95 | 40.33 | 51.25 | 12.8 |
| 2 | 2% glycerol | 30.97 | 51.68 | 49.91 | 16.7 |
| 3 | 4% glycerol | 31.16 | 53.66 | 54.90 | 19.5 |
| 4 | glu:gly(1:1) | 38.97 | 42.23 | 50.72 | 15.0 |
| 5 | glu:gly(1.5:0.5) | 41.24 | 41.22 | 46.10 | 13.4 |
| 6 | glu:gly(0.5:1.5) | 32.38 | 49.14 | 43.40 | 16.3 |
| 7 | glu:gly(0.5:3.5) | 33.63 | 49.88 | 48.92 | 18.7 |
| 8 | glu:gly(1:1) sequential | 31.95 | 51.33 | 40.22 | 14.8 |

4. Nitrogen Sources

Different ratios of inorganic and organic nitrogen sources were tested for the growth of PB31. For inorganic nitrogen, the inventors of the present invention varied sodium nitrate, ammonium chloride, and MSG concentration in the medium to determine their effect on biomass and DHA productivity. For organic nitrogen source, the inventors of the present invention varied yeast extract percentage in the medium from 0.1% to 0.3% (w/v). Best biomass productivity and DHA percentage was achieved with 20 mM $NaNO_3$+0.5 mM $NH_4Cl$+0.3% yeast extract+30 mM MSG. However, this condition resulted in least total fatty acid percentage due to the higher total nitrogen amount in the medium used (Table 4).

TABLE 4

Effect of nitrogen source on PB31 lipid productivity and fatty acids profiles in shake flasks.

| Sample | Condition | Total N amount (g/L) | C16:0 (%) | C22:5 n6 (%) | C22:6 n3 (%) | Total fatty acids (%) | Biomass (g/L) |
|---|---|---|---|---|---|---|---|
| 1 | 20 mM NaNO3 0.5 mM NH4Cl 0.3% Yeast extract 30 mM MSG | 1.04 | 37.87 | 8.7 | 44.93 | 40.23 | 15.2 |
| 2 | 10 mM NaNO3 10 mM NH4Cl 0.1% Yeast extract 30 mM MSG | 0.81 | 39.4 | 8.39 | 43.47 | 48.22 | 13.9 |
| 3 | 10 mM NH4Cl 5 mM (NH4)2SO4 0.1% Yeast extract 30 mM MSG | 0.81 | 41.29 | 7.29 | 42.65 | 54.57 | 12.5 |
| 4 | 5 mM NH4Cl 7.5 mM (NH4)2SO4 0.1% Yeast extract 30 mM MSG | 0.81 | 40.95 | 7.98 | 43.19 | 52.63 | 13 |

5. Wastewater as a Carbon Source

2 L of wastewater, derived from water used to wash dried grapes and containing about 2-4% glucose, was obtained from Lion Raisins (Selma, CA). PB31 was grown using raisin wastewater under different conditions to compare its growth against the base growth medium. The tested conditions were as below.

1) Base growth cell medium+2% (w/v) glucose
2) Wastewater+$NaNO_3$ (same concentrations as in #1)
3) Wastewater (RW) only (raisin wastewater)
4) 25% (v/v) wastewater (25% of wastewater+75% base growth medium)
5) 50% (v/v) wastewater (50% of wastewater+50% base growth medium)
6) 75% (v/v) wastewater (75% of wastewater+25% base growth medium)

The cell culture was grown for 4 days in a 6-well plate and the growth was monitored by measuring the light density of cell cultures on day 3 and day 4.

PB31 growth on raisin wastewater was comparable to the growth on regular medium. A mixture of base growth medium and 25-50% (v/v) raisin wastewater resulted in the highest growth indicating the possibility of wastewater utilization in large-scale fermentation of PB31 (FIG. 8).

IV. Mutagenesis

PB31 cells were subjected to random mutagenesis using UV light followed by Triclosan treatment to improve growth rate and lipid production. Four 10 ml cultures of PB31 in the logarithmic growth phase were placed on Petri dishes and placed 10-15 cm away from UV light bulb in a biosafety hood for 14-60 minutes. 1 ml from each condition was diluted in 1:10,000 with base growth medium and spread onto agar plates containing 1-10 mM Triclosan. About 3-5 colonies were picked from each plate and grown on 6 well plates. The growth rate was monitored by measuring light density at 750 nm while glucose consumption was monitored by measuring light density at 340 nm using a UV spectrophotometer.

3 samples showed faster glucose consumption and growth rate. These strains were designated as PB31-2, PB31-4, and PB31-5. The mutagenized strains also produced higher amounts of lipid and DHA compared to the wild-type cell in the flask and 5 L fermenter experiments (Tables 5 and 6).

TABLE 5

Growth measured by light density and glucose assay results showing remaining levels of glucose in the cell culture media.

| Samples | Optical Density (750 nm) | Remaining glucose (g/L) |
|---|---|---|
| 1 | 9.22 | 12.69 |
| 2 | 10.94 | 3.15 |
| 3 | 7.9 | 11.81 |
| 4 | 11.28 | 2.85 |
| 5 | 11.2 | 0.97 |
| 6 | 6.86 | 11.74 |
| 7 | 8.26 | 11.28 |
| 8 | 8.28 | 11.03 |
| 9 | 7.28 | 12.68 |
| 10 | 8.26 | 11.53 |
| 11 | 7.36 | 11.17 |
| 12 | 7.1 | 13.36 |

TABLE 6

Lipid profiles of mutagenized cells in flasks and 5 L fermenter experiments.
Fatty acids (%)

| Samples | flask experiment (5 days) | | | 5 L fermenter (5 days) | |
|---|---|---|---|---|---|
| | C16:0 (Palmitic) | C22:5 (n6) (DPA) | C22:6 (n3) (DHA) | DHA | Total oil |
| PB31-2 | 42.75 | 6.96 | 41.72 | 34.93 | 47.39 |
| PB31-4 | 43.04 | 6.82 | 40.34 | 38.66 | 70.51 |

TABLE 6-continued

Lipid profiles of mutagenized cells in flasks and
5 L fermenter experiments.
Fatty acids (%)

| | flask experiment (5 days) | | | 5 L fermenter | |
| | C16:0 | C22:5 | C22:6 | (5 days) | |
| Samples | (Palmitic) | (n6) (DPA) | (n3) (DHA) | DHA | Total oil |
|---|---|---|---|---|---|
| PB31-S | 39.5 | 7.25 | 44.32 | 30.8 | 65.53 |
| P831 control | 54.54 | 4.99 | 32.2 | 22.67 | 54.88 |

Fed-Batch 5000 L Fermentation and Optimization of PB3144.

PB31-4 was grown for 5 days in 5000 L commercial-scale fermenters custom-fitted with low irradiance light strips to provide PSP conditions. Large-scale fermenter media consisted of the following in ranges in 1 L water: 13-17 g $Na_2SO_4$, 1.5 g NaCl, 3-6 g $MgSO_4$ $7H_2O$, 0.3 g $CaCl_2$), 1.7 g $NaNO_3$, 3-5 g yeast extract, 12-20 g MSG, 0.027 g $NH_4Cl$, 10-20 ml stock trace metal solution, 1-2 ml chelated iron solution, 80 ml 0.1M Phosphate solution (pH7.8) and 4 ml vitamin solution. Stock trace metal solution consisted of the following in 100 ml: 0.1 g $Na_2EDTA$ $2H_2O$, 0.114 g $H_3BO_3$, 4.9 mg $FeCl_3$ $6H_2O$, 1.92 mg $MnCl_2$ $4H_2O$, 2.2 mg $ZnSO_4$ $7H_2O$, and 0.48 mg $CoCl_2$ $6H_2O$. The stock chelated iron solution consisted of the following in 100 ml: 0.5 g $Na_2EDTA$, 10 ml 1M HCl solution and 0.081 g $FeCl_3$ $6H_2O$. Sterile stock vitamin solution consisted of the following in 200 ml: 50 mM HEPES (pH7.8), 0.44 g Thiamine-HCl, 0.005 g Biotin, 0.027 g B12 and 0.619 g D-Pantothenic acid hemicalcium. Stock phosphate solution consisted of the following in 1 L: 90.8 ml 1M $K_2HPO_4$ and 9.2 ml 1M $KH_2PO_4$. pH was adjusted using 8% NaOH, 8% KOH and 10% $H_2SO_4$ solutions. 50 ppm antifoam was used to control bubbles and foams produced during fermentation. The dissolved oxygen level was kept below 1 during the lipid production steps.

Results from eighteen runs of PB31-4 in large-scale fermenters, shown in table 7, demonstrate consistent production of over 70% by weight total oil in biomass and 45% by weight DHA oil.

TABLE 7

PB31-4 scale-up in 5000 L large-scale fermenters.

| Runs | Total biomass (g/L) | Total oil (%) in biomass | Total DHA (%) |
|---|---|---|---|
| 1 | 59.65 | 75.93 | 45.68 |
| 2 | 64.19 | 76.05 | 48.78 |
| 3 | 64.92 | 78.5 | 45.88 |
| 4 | 63.07 | 77.59 | 45.62 |
| 5 | 67 | 79.08 | 44.09 |
| 6 | 63.27 | 76.88 | 44.11 |
| 7 | 61.84 | 76.91 | 45.31 |
| 8 | 64.78 | 75.99 | 45.51 |
| 9 | 62.36 | 73.09 | 46.11 |
| 10 | 63.29 | 73.06 | 45.6 |
| 11 | 62.71 | 76.05 | 44.49 |
| 12 | 61.99 | 74.81 | 45.19 |
| 13 | 66.88 | 77.28 | 46.23 |
| 14 | 67 | 77.41 | 46.29 |
| 15 | 66.13 | 76.86 | 44.99 |
| 16 | 67.19 | 77.07 | 45.56 |

Lipid Extraction and Fatty Acid Profiles

Total lipid was extracted from freeze-dried cell pellets grown in a 250 ml flask. About 2 g sample in 50 ml falcon tube was treated with 5 ml HCl acid in 80° C. water bath for about 1 hour with occasional shaking. After the sample cooled down, 35-40 ml of ethyl ether was added to the falcon tube, followed by vortexing and centrifugation at maximum rpm. The upper solvent layer was collected in a round bottom flask. Extraction with ethyl ether was carried out 2 more times. 30 ml petroleum ether was added to the falcon tube, followed by vortexing and centrifugation. The upper solvent layer was collected and the ether solvent in the round bottom flask was evaporated using a rotavapor.

25 mg of extracted oil was transferred to a 5 ml glass vial. 1 ml Isooctane and 2 ml 14% Boron trifluoride (BF3) were added to the sample followed by incubation on a 100° C. heat block for an hour. Cooled down methylated oil sample was transferred to a 15 ml falcon tube after adding 5 ml saturated NaCl solution and 1 ml Isooctane. Following vortexing and centrifugation, the upper oil layer was collected in a microtube for GC chromatography. The sample was then analyzed using the Agilent Technologies 7890A GC system.

Fatty acids extracted from PB31 cells are mainly composed of palmitic acid and DHA. Palmitic acid accounts for nearly 51% of total fatty acids (TFA) while DHA accounts for the remaining 49% of TFA. Palmitic acid and DHA are also the dominant fatty acids produced by *S. limacinum* (Yokochi et al., 1998), *S. mangrovei* (Fan et al., 2001), *T. aureum* (Bajpaj et al., 1991; lida et al., 1996), and *Thraustochytrium* sp. (Singh et al., 1996).

For a more concentrated higher volume fermentation product (5000 L), PB31 was grown under PSP conditions to produce the maximum amount of algal bioproducts. Cultivation methods such as traditional heterotrophic fermentation, closed photo-bioreactor, or open pond system can be used to culture PB31 at large scale. Algae culture can be harvested by using centrifugation, flocculation, floatation, or filtration. After an algal product is harvested, several drying methods such as a spray dryer and drum dryer can be utilized to get algal powder. Algae culture can be used directly without harvesting the algal sludge before the drying step depending on which drying method will be employed for the specific application. The supercritical fluid extraction method is used for 5000 L fermenter products but organic chemical solvents such as Soxhlet or hexane extraction, or mechanical methods such as expeller press, or ultrasonic-assisted extraction can be used to extract total oil product from the algal powder.

PB31 cells are made up of 40-80% fat, 5-40% carbohydrates, and 10-50% proteins. Algae products such as extracted oil including hydrocarbons, carotenoids, and further purified omega-3 and/or 6 fatty acids can be used as processed materials for food ingredients (especially for chocolates) and additives, nutraceuticals, pharmaceuticals, and cosmetic ingredients. Algal powders can be used for animal feed (specifically adding or mixing into feeds for cows, pigs, chickens, goats, sheep, and pet food) and for aquatic animals without further processing, purification, or treatment steps. Besides animal feed, carbohydrates, and proteins from algae (such as dietary fibers and polysaccharides, oligo peptides, protein extracts, and essential fatty acids) can be used in cosmetics, bio-plastic materials, and functional ingredients such as algal flour, vitamins, and minerals.

V. Metabolic Engineering

1. Transformation and Recovery of PB31 Recombinant Strains.

Establishing a versatile and reproducible transformation system is a key first step towards modulating the production of various bio-products in PB31. EF1a is one of the most highly expressed genes in *Thraustochytrids*. To take advantage of its high expression, the inventors of the present invention attempted to use this locus as a landing pad for transformation into PB31 nuclear genome and co-opt EF1a promoter and 3' untranslated regions for driving the expression of various marker genes. This was achieved by disrupting or knocking out the endogenous EF1a gene and replacing it with neomycin, sucrose invertase, or bleomycin marker genes.

This example describes recombinant strains recovered following the transformation of PB31 with plasmids pPB0128, pPB0136, and pPB0240 containing *S cerevisiae* neomycin resistance gene, *S. cerevisiae* sucrose invertase gene, and *S. hindustanus* bleomycin gene respectively under the control of Elongation factor 1 alpha promoter and terminator regions amplified from PB31 genomic DNA.

Specific primers, based on the genomic sequences of closely related strains in the GenBank database, were used to amplify about 1500 kb Elongation factor 1 alpha (EF1a) gene region from PB31. The purified PCR product was cloned using pJET1.2/blunt vector (Fisher Scientific, USA). Extracted plasmid DNA from 3-5 clones was sequenced to verify the amplified region. Sequences from each clone of the PB31 EF1α region showed several polymorphisms in the upper 5' flanking regions of the gene coding sequence as well as in the downstream 3' flanking regions from the reference strains. Based on the PB31 EF1α region sequences, the inventors of the present invention decided to use about 1000 bp of EF1α promoter and terminator regions as potential recombination flanks in our PB31 transformation experiments.

Protein sequences of neomycin resistance and sucrose invertase genes from *S. cerevisiae* and bleomycin resistance gene from *Streptoalloteichus hindustanus* were downloaded from the public GenBank database. The protein sequences were codon optimized for optimum expression in PB31 using codon tables of several publicly available and closely related thraustochytrid species. Optimized gene fragments were synthesized using an outside vendor (Genewiz Inc, San Francisco, CA USA). Plasmid DNA, extracted from *E. coli* transformed with the synthesized neomycin, sucrose invertase, or bleomycin genes cloned into pJET1.2/blunt vector, was sequenced to confirm the original sequences.

PB31 EF1α promoter and terminator elements driving neomycin resistance gene were assembled into BamHI cut PUC19 vector using NEB assembly master mix (New England Biolabs, USA) and designated as pPB0128. Construct pPB0128 for transformation into PB31 can be written as pPB0128-PB31EF1a::neoR(s)::PB31EF1a The sequence of the transforming DNA contained in pPB0128 is shown in FIG. 9. Two BamHI restriction sites used to generate linear DNA for the transformation of the cassette into PB31 are indicated in lowercase bold at the beginning and the end of the sequence. Underlined sequences at 5' and 3' flanks of the construct represent genomic DNA from PB31 that enables targeted integration of the transforming DNA via homologous recombination at the EF1α region. The 5' flank also acts as the promoter region for driving the expression of downstream neomycin resistance gene, codon optimized for expression in PB31, allowing the strains to grow in presence of neomycin selection. The initiator ATG and terminator TGA for the ScNeo[R] gene are indicated in uppercase italics, while the coding region is indicated with lowercase italics. Immediately following the ScNeo[R] is the underlined 3' flank of EF1α which contains the terminator region of the gene as well.

The inventors of the present invention also generated plasmids pPB136 and pPB240 containing either sucrose invertase or bleomycin as the marker genes. These constructs can be written as:

pPB0136-PB31EF1a::ScSUC2::PB31EF1a
pPB0240-PB31EF1a::ble::PB31EF1a pPB0136 and pPB0240 have same 5' and 3' EF1a flanking sequences as pPB0128 except that they contain either sucrose invertase (pPB0136) or bleomycin gene (pPB0240) marker genes instead of neomycin sandwiched between the PB31 EF1a flanks. The sequence of sucrose invertase and bleomycin genes contained in plasmids pPB0136 and pPB0240 is shown in FIGS. 10 and 11 respectively.

Plasmids pPB0128, pPB0136, and pPB0240 were introduced into PB31 by modified lithium acetate (LiAc) transformation method. Briefly, 50 ml PB31 cell cultures grown overnight in growth medium were harvested by centrifugation and washed with 5 ml wash solution (0.1M LiAc and 1× Tris EDTA (pH8.0). The cell culture was centrifuged at 3750 rpm and the supernatant was discarded. Cell pellet was resuspended with a 500 ml-1000 ml wash solution and incubated at room temperature on an orbital shaker for 1 hour. 150 ml cell suspension was transferred to a sterile Eppendorf tube containing 12-15 μg sterile, digested DNA and incubated at room temperature for 30 minutes on an orbital shaker. A mock transformation without DNA was also setup as a control. A 750 μl PEG solution (0.1M LiAc+1×TE+40% PEG-4000) was added to the Eppendorf tube and incubation at room temperature on the orbital shaker was continued overnight. Following overnight incubation, cells were harvested by centrifugation. Optionally, before harvesting cells, overnight incubated cells could be further incubated in 42° C. water bath for 10-15 minutes. 100-180 μl growth medium was added to the cells after the supernatant was discarded. Primary transformants were selected for heterotrophic growth on media containing proper selection depending on the construct introduced. Cells transformed with pPB0128 (containing neomycin resistance gene) and pPB0240 (containing bleomycin gene) were spread onto agar plates containing glucose as the carbon source with neomycin or zeocin selection using glass beads. Cells transformed with pPB0136 (containing sucrose invertase gene) were spread on agar plates containing sucrose as the sole carbon source.

Colonies started to appear on plates containing cells transformed with pPB0128 and pPB0240 after 2-3 days while colonies on plates containing pPB0136 took more than 10-14 days. No colonies were formed on plates containing mock-transformed cells. The below table summarizes the results from various transformations of PB31 with pPB0128, pPB0136, and pPB0240 (Table 8).

TABLE 8

| Colonies formed per plate following transformation of PB31 with pPB0128, pPB0136, and pPB0240. PB31 transformation efficiency | |
| --- | --- |
| Gene marker | Colonies per plate |
| Neomycin resistance gene | 15-20 |
| Bleomycin gene | 1-40 |
| Sucrose invertase gene | 1-4 |

Single colonies were clonally purified and insertion of the various marker genes at EF1α locus was verified by PCR amplification and sequencing of the regions flanking the integration site.

Disruption of EF1α gene had no noticeable impact on the growth pattern in engineered PB31 suggesting that this locus could be used as a neutral site for integrating heterologous gene cassettes to modulate fatty acid composition in subsequent experiments.

The above example established several facts summarized below:

1. PB31 can be efficiently and reproducibly transformed using a modified LiAc transformation method described in our example.
2. Homologous recombination occurs in PB31 and can be used as a tool to modulate various enzyme activities by gene knockdowns, knockouts, and knock-ins.
3. Homologous recombination in PB31 can be used to enhance or suppress a target gene activity by replacing endogenous regulatory elements with up-or down-regulated heterologous regulatory elements,
4. Specific point mutations can be introduced into endogenous enzymes to affect an alteration in the catalytic activity of target enzymes resulting in an enhanced product profile or even novel products, and
5. An optimum combination of 2-4 will yield novel product profiles in PB31.

2, Disrupting Fatty Acid Synthase Gene in PB31 Results in Enhanced PKS-Dependent Accumulation of DPA and DHA After having established a robust PB31 transformation method, we next endeavored to modulate the polyunsaturated fatty acid levels in PB31 and decided to disrupt the fatty acid synthase (FAS) gene in PB31 with neomycin resistance marker.

This example describes constructing a recombinant plasmid pPB0152 containing fatty acid synthase region amplified from PB31 and *Saccharomyces cerevisiae* neomycin resistance gene (neoR) coupled with PB31 Elongation factor 1 alpha terminator gene fragments amplified from pPB0128 (example 1 above).

Using primers based on the genomic sequences of closely related strains in the Genbank database, upper 5' flanking regions of the fatty acid synthase (FAS) gene coding region was amplified from the PB31 strain. The purified PCR product was then cloned using pJET1.2/blunt vector (Fisher Scientific, USA). Extracted plasmid DNA from 3-5 clones was sequenced to verify the amplified region. Sequences from each clone of the PB31 FAS region showed several polymorphisms in the upper 5' flanking regions of the gene coding sequence as well as in the downstream 3' flanking regions from the reference strains and from the PB31 clones indicating 2 copies of FAS gene with several polymorphic bases in the upper 5' flanking region. pPB0152 was constructed to disrupt and down-regulate the expression of PB31 FAS gene. Based on the PB31 upper 5'flank FAS region sequences, about 852 bp of 5'flank FAS region was designated as the promoter for allele 1 and about 1013 bp of as the promoter for allele 2. We also amplified an 804 bp FAS 3'flank region 500 bp downstream from the start of translation of the FAS gene, so that the final construct (pPB0152) contained FAS allele 1 as the 5'' flank and 804 bp downstream FAS flank as the 3'flank thereby deleting 500 bp from the FAS coding region and disrupting it upon transformation and integration into the PB31 genome. Plasmid pPB0152 was constructed by assembling 852 bp FAS allele1, neomycin resistance gene, EF1 alpha terminator region, and the FAS 3' flank into pUC19 cloning vector containing (BamH1) restriction sites using the NEB assembly master mix (New England Biolabs, USA). 852 bp PB31 FAS 5' flank acted as the promoter driving the downstream expression of neomycin resistance gene. The final pPB0152 construct can be written as:

pPB0152-PB31 FAS 5' flank::Neo(R)-EF1α terminator:: PB31 FAS 3' region

FIG. 12 describes the sequence of plasmid construct pPB0152 with BamH1 restriction site, used for cloning and generating linear DNA for transformation, indicated in lowercase bold. Uppercase underlined sequences at the beginning and the end of the construct represent the PB31 allele 1 FAS 5' flank and PB31 FAS 3' flank that enable targeted integration of the transforming DNA via homologous recombination at the FAS locus allowing disruption of allele 1 of PB31 FAS gene. Proceeding in 5' to 3' direction, the PB31 FAS 5' flank acts as a promoter driving the expression of the neomycin resistance gene indicated in lowercase italics. The initiator ATG and terminator TGA for neo(R) are indicated in uppercase italics. Neomycin coding sequence is immediately followed by terminator region from PB31 EF1 alpha in small capitals. The PB31 FAS 3' flanking region (part of FAS CDS) is indicated in the uppercase underlined letters. The final construct was sequenced to ensure correct reading frames and targeting sequences.

To determine its impact on fatty acid profiles, pPB0152 was transformed into PB31 and primary transformants were selected on growth media containing neomycin. Single clonally purified colonies were grown under standard lipid production conditions in shake flasks. The fatty acid profiles of lipids from shake flask assays of representative derivative lines arising out of the transformation of wildtype PB31 with pPB0152 are shown in Table 9.

TABLE 9

Fatty acid profiles as a percentage of total fatty acids from representative derivative PB31 lines transformed with plasmids pPB0152.

| | Fatty Acids (%) | | | | | |
| --- | --- | --- | --- | --- | --- | --- |
| Sample name | C14:0 Myristic | C16:0 Palmitic | C18:0 Stearic | C20:5n3 EPA | C22:5n6 DPA | C22:6n3 DHA |
| PB31 parent | 2.83 | 55.14 | 1.6 | 0.69 | 5.54 | 33.28 |
| PB31; 152-1 | 1.83 | 52.27 | 1.83 | 0.72 | 7.8 | 35.55 |
| PB31; 152-2 | 1.49 | 54.57 | 1.82 | ND | 6.91 | 35.21 |
| PB31; 152-3 | 1.7 | 47.22 | 1.54 | ND | 8.48 | 40.27 |

ND - not detected

Disruption of FAS allele 1 in PB31 resulted in subtle but noticeable changes in the fatty acid profile in the derivative transgenic lines. Representative derivative lines PB31; 152-1, PB31; 152-2, and PB31; 152-3 showed an increase in DPA (C22:5n6; 7.8%, 6.91%, and 8.48% respectively vs 5.54% in wildtype PB31) and DHA (C22:6n3; 35.55%, 35.21%, and 40.27% respectively vs 33.28% in wildtype PB31). The increase in DPA and DHA came at the expense of C14:0 and C16:0 which showed consistent decrease in all the representative derivative lines. Significant reduction in C14:0 and C16:0 in PB31; 152-3 manifested as the highest DPA and DHA seen in this set of derivative lines compared to wildtype PB31. This data provides a strong indication that disrupting FAS gene in PB31 results in reduced C16:0 synthesis in derivative lines with a concomitant increase in PKS-derived DPA and DHA. PB31; 152-1 and PB31; 152-3 were banked as Phycoil engineered strains PES-100 and PES-101 respectively.

3. Introducing Specific Point Mutations into Polyunsaturated Fatty Acid Synthase (Pfs) B Gene in PB31 Results in Recombinant Strains Producing Low or No C22:5n6

About 1500 bases upstream region and part of polyunsaturated fatty acid synthase (Pfs) B coding region was amplified from PB31 genomic DNA. The amplified PCR product was purified and ligated into a blunt vector (pJET1.2) and transformed into competent cells. Plasmid DNA was extracted and sequenced to compare and confirm the locus from the reference genomic sequence from Genbank. Three point mutations were introduced into the coding sequence of Pfs B to alter specific amino acids. The first mutation was introduced to convert phenylalanine at 65 bases from the starting translation point to leucine (F65 L) and second mutation was introduced to phenylalanine at 230 bases from the start of translation to leucine (F230 L) and the third mutation was introduced to isoleucine at 231 bases from the start of translation to threonine (I231T). These mutations when introduced into *Aurantiochytrium* sp. OH4 DHA synthase gene were recently reported to kickstart EPA production in a heterologous *E. coli* host (Hayashi et al., 2019). However, the functionality and specificity of these mutations to produce EPA in a thraustochytrid host have not been demonstrated. We endeavored to test the effect of these mutations in our PB31 thraustochytrid host strain and constructed a plasmid pPB0218 for this purpose. Construct pPB218 introduced for expression in PB31 can be written as pPB0218-PB31_4-2 pfsBp 5'flank:ScNeo-ApBicistronic signal:PB31_4-2 PfsB F65 L F230 L I231T ORF 3' flank.

The sequence of the plasmid pPB0218 is shown in FIG. 13. NotI restriction endonuclease site used to generate linear DNA and for cloning is indicated in lowercase bold and delimits 5' and 3' ends of the transforming DNA. Underlined uppercase text at 5' and 3' flanks of the construct represent genomic DNA from Thraustochytrid PB31 that enable targeted integration of the transforming DNA via homologous recombination at the pfs B allele 2 locus. The 5' flank acts as the promoter driving the expression of downstream neomycin phosphotransferase II gene (Neo, codon-optimized for expression in *A. protothecoides* and encoding neomycin phosphotransferase II, thereby enabling the strain to grow on aminoglycoside antibiotic G418). The initiator ATG and terminator TGA for Neo are indicated in uppercase italics while the rest of the sequence is indicated in lowercase italics. The neomycin coding sequence is followed by 101 nucleotide sequence from *A. protothecoides*, in small capitals, to act a bicistronic signal allowing production of neomycin and mutated Pfs B allele 2 protein from a single transcript. Immediately, following this bicistronic sequence is 3' pfs B flank containing the F65 L, F230 L, and I231T mutations. The final construct was sequenced to ensure correct reading frames and targeting sequences. Once transformed and integrated into PB31 genome, we envisaged that Pfs B protein with intended modifications will be produced in recombinant strains selected on neomycin resistance.

pPB0218 was transformed into PB31 thraustochytrid strain and the primary transformants were selected growth media supplemented with G418. Single clonally purified colonies were grown under standard lipid production conditions in shake flasks. The resulting profiles from a set of representative derivative clones arising from transformations with the construct pPB0218 are shown in Table 10.

TABLE 10

Fatty acid profiles as a percentage of total fatty acids from representative derivative PB31 lines transformed with plasmids pPB0218.

| Sample name | Fatty Acids (%) | | | | | |
|---|---|---|---|---|---|---|
| | C14:0 Myristic | C16:0 Palmitic | C18:0 Stearic | C20:5n3 EPA | C22:5n6 DPA | C22:6n3 DHA |
| PB31 control | 2.33 | 54.58 | 1.66 | 0.55 | 5.39 | 34.87 |
| PB31; 218-1 | 3.87 | 57.8 | 1.31 | 0.45 | 1.89 | 31.36 |
| PB31; 218-2 | 2.88 | 54.54 | 1.69 | 1.06 | 1.45 | 35.43 |
| PB31; 218-4 | 3.54 | 55.55 | 1.33 | 0.49 | 3.30 | 32.22 |
| PB31; 218-5 | 2.81 | 60.11 | 2.03 | 1.07 | 1.16 | 31.69 |
| PB31; 218-9 | 3.03 | 58.5 | 1.72 | 0.88 | 0.95 | 32.17 |
| PB31; 218-13 | 3.68 | 63.15 | 1.85 | 0.46 | 0.86 | 27.24 |

Introducing F65 L F230 L I231T mutations in the Pfs B allele 2 in PB31 did not result in the enhanced accumulation of EPA in derivative transgenic strains (table 10) contrasting the reported results obtained in heterologous host *E. coli* (Hayashi et al., 2019). However, there was a significant reduction in the DPA in all the derivative transgenic lines. Except PB31; 218-4, which produced 3.3% DPA, all the derivative transgenic lines produced less than 2% of DPA compared to 5.3% DPA in PB31 parent. PB31; 218-5, PB31; 218-9, and PB31; 218-13, produced the lowest amounts of DPA (1.16%, 0.95% and 0.86% respectively) compared to control PB31. Except for PB31; 218-13, there was very subtle decrease in DHA in the derivative lines concomitant with a slight increase in C16:0 levels. In derivative line PB31; 218-13, significant decrease in DPA and DHA levels was strongly associated with an increase in C16:0. These resulted demonstrate that F65 L F230 L and I231T mutations can modulate Pfs B activity in PB31 resulting in DHA oils containing very low amounts of DPA. PB31; 218-5 producing 1.16% of DPA was banked as Phycoil engineered strain PES-102 and used as the parent strain in the subsequent experiments.

Since pPB0218 was targeted to introduce F65 L F230 L and I231T mutations at Pfs B allele 2, we hypothesized that the non-mutated allele 1 of Pfs B more than likely accounts for the remaining DPA seen in the derivative transgenic lines. In an attempt to further lower the DPA levels, we made another construct (pPB0258) introducing the same F65 L F230 L and I231T mutations at Pfs B allele 1. For this construct we used bleomycin gene from *Streptoalloteichus hindustanus* as a selectable marker. Construct pPB0258 can be written as:

pPB0258-PB31_4-1 pfsBp 5'flank:ble-ApBicistronic signal:PB31_4-2 PfsB F65 L F230 L I231T ORF 3' flank The sequence of the plasmid pPB0258 is shown in FIG. 14. NotI restriction endonuclease site used to generate linear DNA and for cloning is indicated in lowercase bold and delimits 5' and 3' ends of the transforming DNA. Underlined uppercase text at 5' and 3' flanks of the construct represent genomic DNA from Thraustochytrid PB31 that enable targeted integration of the transforming DNA via homologous recombination at the pfs B allele 1 locus. The 5' flank acts as the promoter driving the expression of downstream bleomycin (Ble, codon-optimized for expression in PB31 and enabling the strain to grow on zeocin selection). The initiator ATG and terminator TGA for Ble are indicated in uppercase italics while the rest of the sequence is indicated in lowercase italics. The bleomycin coding sequence is followed by 101 nucleotide bicistronic signal from *A. protothecoides*, in small capitals, allowing production of both bleomycin and mutated Pfs B allele 1 proteins from a single transcript. Immediately, following this bicistronic sequence is 3' pfs B flank containing the F65 L, F230 L, and I231T mutations. The final construct was sequenced to ensure correct reading frames and targeting sequences.

pPB0258 was transformed into PES-102 strain and the primary transformants were selected on growth media supplemented with G418 and zeocin. Single clonally purified colonies were grown under standard lipid production conditions in shake flasks. The resulting profiles from a set of representative derivative clones arising from transformations with the construct pPB0218 are shown in Table 11.

TABLE 11

Fatty acid profiles as a percentage of total fatty acids from representative derivative PES-102 lines transformed with plasmids pPB0258. The derivative transgenic samples PES-102; 218-2 and PES-102; 218-3 were run twice to confirm the results.

| | Sample name | C14:0 Myristic | C16:0 Palmitic | C18:0 Stearic | C20:5n3 EPA | C22:5n6 DPA | C22: 6n3 DHA |
|---|---|---|---|---|---|---|---|
| | | | | | Fatty Acids (%) | | |
| Run 1 | PB31 Wildtype | 2.75 | 57.52 | 1.62 | ND | 5.1 | 32.67 |
| | PES-102 Parent | 2.88 | 59.48 | 1.76 | 0.95 | 1.1 | 32.16 |
| | PES-102; 258-2 | 2.73 | 59.11 | 1.82 | 1.58 | ND | 32.99 |
| | PES-102; 258-3 | 3.38 | 62.44 | 1.75 | 1.23 | ND | 29 |

TABLE 11-continued

Fatty acid profiles as a percentage of total fatty acids from representative derivative PES-102 lines transformed with plasmids pPB0258. The derivative transgenic samples PES-102; 218-2 and PES-102; 218-3 were run twice to confirm the results.

| | Sample name | C14:0 Myristic | C16:0 Palmitic | C18:0 Stearic | C20:5n3 EPA | C22:5n6 DPA | C22: 6n3 DHA |
|---|---|---|---|---|---|---|---|
| | | | | | Fatty Acids (%) | | |
| Run 2 | PES-102; 258-2 | 2.49 | 59.89 | 1.93 | 1.42 | ND | 32.46 |
| | PES-102; 258-3 | 2.48 | 61.44 | 1.99 | 1.73 | ND | 31.59 |

ND - not detected

As hypothesized, F65 L F230 L and I231T mutations introduced into both alleles of Pfs B resulted in strains with almost no DPA. The DPA peak seen in PES-102; 258-2 and PES-102; 258-3 was below the detection level of the GC and did not translate into a measurable number (Table 10). We ran the PES-102; 258-2 and PES-102; 258-3 derivative lines a second time, and similar results were obtained. Taken together, our data demonstrate that F65 L F230 L and I231T mutations introduced into Pfs B protein in Thraustochytrid PB31 can modulate the polyketide synthase (PKS) system such that DHA oils with very low or no DPA can be generated on demand. We expect to further fine tune this capability of producing DHA oils with tailored DPA amounts (between 0-5%) by controlling fermentation conditions at scale. PES-102; 258-2 and PES-102; 258-3 were banked as Phycoil engineered strains PES-103 and PES-104 respectively.

The work presented above demonstrates our ability to produce novel LCPUFAs by manipulating both FAS and PKS systems.

What is claimed is:

1. A method of preparing a bio-oil, the method comprising the steps of:

(1) culturing *Schizochytrium* sp. PB31 having ATCC accession number PTA-123692, wherein the *Schizochytrium* sp. PB31 having ATCC accession number PTA-123692 comprises a disruption of a Pfs B; and (2) collecting a cultured cell biomass and (3) extracting and separating the bio-oil containing an omega-3 polyunsaturated fatty acid or an omega-6 polyunsaturated fatty acids.

2. The method of claim 1, wherein the bio-oil comprises 30 to 55 wt % polyunsaturated fatty acid based on total fatty acids.

3. The method of claim 1, wherein the culturing of step (1) is a batchwise culturing, a fed-batchwise culturing, or a continuous culturing.

4. The method of claim 1, further comprising disrupting the cultured cell biomass.

5. The method of claim 1, further comprising the step of purifying the bio-oil containing the polyunsaturated fatty acid.

6. The method of claim 2, wherein the cultured cell biomass contains 70 to 80 wt % of lipid.

7. The method of claim 1, wherein the culturing is a heterotrophic fermentation.

8. The method of claim 1, wherein the culturing step includes use of a light having a light intensity of less than 5 $\mu mol/m^2/s$.

9. The method of claim 8, wherein the light signal is generated by a continuous light or a discontinuous light.

10. The method of claim 8, wherein the light signal is generated by a light having a full spectrum or a light having a specific wavelength.

11. The method of claim 1, wherein the culturing is performed using a medium containing a carbon source and a nitrogen source.

12. The method of claim 11, wherein the carbon source is selected from the group consisting of a glucose, a fructose, a galactose, a mannose, a sucrose, an arabinose, a xylose, a sodium acetate, and a glycerol.

13. The method of claim 1, wherein the bio-oil contains an ARA, an EPA, a DPA, or a DHA.

14. The method of claim 13, wherein the bio-oil contains an ARA.

15. The method of claim 13, wherein the bio-oil contains an EPA.

16. The method of claim 13, wherein the bio-oil contains a DPA.

17. The method of claim 13, wherein the bio-oil contains a DHA.

18. The method of claim 13, wherein the cultured cell biomass contains 70 to 80 wt % of lipid.

19. The method of claim 18, wherein the bio-oil comprises 30 to 55 wt % polyunsaturated fatty acid based on total fatty acids.

20. The method of claim 19, further comprising the step of purifying the bio-oil containing the polyunsaturated fatty acid.

* * * * *

SEQUENCE LISTING

```
Sequence total quantity: 10
SEQ ID NO: 1              moltype = DNA  length = 1296
FEATURE                   Location/Qualifiers
misc_feature              1..1296
                          note = PB31 18S rRNA Partial Sequence
source                    1..1296
                          mol_type = other DNA
                          organism = synthetic construct
SEQUENCE: 1
aaagatggga tcacagagta gtgactctgt ccagattgaa tccaaacaga aacatcccat  60
ggtttcatcg gaccgttcaa tcggtaggtg cgacgggcgg tgtgtacaaa gggcagggac  120
gtattcaatg caagctgatg acttgcgttt actaggaatt cctcgttgga gattaataat  180
tgcaaaaatc tagccccagc acgatgagcg ttccaaggat tagccaggcc ttccgaccaa  240
gcactcaatt ccataaaata aaatttaaac ccgatgaacc cctccatgga acgcgcgggg  300
ggcccaaaaa atccaagggc atcccaaacc tggtattggc cccaacttcc tggccgtaaa  360
ccggaaatgg ccctccaaaa aattaaaaac gactaagttt gcctaacccg ccctatttta  420
taaggccagg gcccctttct ttaaggaaat taaccaaaaa atcccccccc ccaataaaaa  480
agggcctggc ccccccccc aaaaaacctg gaaaaactcc caaaccggcc atcccaacca  540
atgctgggac cgggaaattt ttcccggggtt aatccaattt aaccccaagg tccctcccg  600
gggggggccc ttccgccaat tccttaaatt tcaaccctgg gaacatactc cccccggaaa  660
cccaagaaat ttaattctca agtgcgggcg gcgaaggccc ttaaaaaacc cccccaaacc  720
caaatcgcgt tcttttacgg gtaaaaaaaa aggggtccaa actctttat ccccaaattt  780
tttttttgtt atagaaacat ggctgggaaa agccctcccc caaatgtgcc tttcggaaat  840
ccaaaaattt cccttcacc cccaaaaaca aaaaccccca ctggtccaat aaccataacc  900
aggggggaaa caaaaaaaaa gacccagtc ctattttact ccccaaaaaa aataaccggt  960
taagaaccgg ttggaaacct cggtttgtta caggggaaag ttccccctt aaagaaagga  1020
aaaatgggcc ggggaccggg aaactttccc cttccgggaa aaccggggcc ctgcgggaaa  1080
ttacaaaaag gctttaatgg ccaactttca agggtcgggg aggggaatcc cgggttgggc  1140
ccaaattttc cctttttttc cttaaagggt ttattgggtt tttcttggaa aaaaaaaaaa  1200
acccccccaa aattttttccc cccctccgg gaaccaaagg gaattaaacc ccgggttcct  1260
ttagggaaag gcccttttt ccctttttgga gaaaac                            1296

SEQ ID NO: 2              moltype = DNA  length = 1757
```

-continued

```
FEATURE              Location/Qualifiers
misc_feature         1..1757
                     note = PB31 consensus 18S rRNA sequence
source               1..1757
                     mol_type = other DNA
                     organism = synthetic construct
SEQUENCE: 2
aacctggttg atcctgccag tagtcatatg ctcgtctcaa agattaagcc atgcatgtgt   60
aagtataagc gattgtactg tgagactgcg aacggctcat tatatcagta ataatttctt  120
cggtagtttc ttttatatgg atacctgcag taattctgga aataatacat gctgtaagag  180
ccctgtatgg ggctgcactt attagattga agccgatttt attggtgaat catgataatt  240
gagcagattg actatttttr gtcgatgaat cgtttgagtt tctgccccat cagttgtcga  300
cggtagtgta ttggactacg gtgrctataa cgggtgacgg agagttaggg ctcgactccg  360
gagagggagc ctgagagacg gctaccatat ccaaggatag cagcaggcgc gtaaattacc  420
cactgtggac tccacgaggt agtgacgaga aatatcgatg cgaagcgtgt atgcgttttg  480
ctatcggaat gagagcaatg taaaaccctc atcgaggatc aactggaggg caagtctggt  540
gccagcagcc gcggtaattc cagctccaga agcatatgct aaagttgttg cagttaaaaa  600
gctcgtagtt gaatttctgg catgggcgac cggtgctttc cctgaatggg gattgattgt  660
ctgygttgcc ttggccatct ttytcwtkyy dttwtwggkr wgaratcttt cactgtaatc  720
aaagcagagt gttccaagca ggtcgtatga ccggtatgtt tattatggga tgataagata  780
ggacttgggg gctattttgt tggtttgcac gcctgagtaa tggttaatag gaacagttgg  840
gggtattcgt atttaggagc tagaggtgaa attcttggat ttccgaaaga cgaactagag  900
cgaaggcatt taccaagcat gttttcatta atcaagaacg aaagtctggg gatcgaagat  960
gattagatac catcgtagtc tagaccgtaa acgatgccga cttgcgattg ttgggtgctt 1020
twttaatggg cctcagcagc agcacatgag aaatcaaagt ctttgggttc cggggggagt 1080
atggtcgcaa ggctgaaact taaaggaatt gacggaaggg caccaccagg agtggagcct 1140
gcggcttaat ttgactcaac acgggaaaac ttaccaggtc cagacatagg taggattgac 1200
agattgagac ctctttcatg attctatggg tggtggtgca tggccgttct tagttggtgg 1260
agtgatttgt ctggttaatt ccgttaacga acgagacctc ggcctactaa atagtgcgtg 1320
gtatgcaac atagtrcgtt tttaacttct tagagggaca tgtccggttt acgggcagga 1380
agttcgaggc aataacaggt ctgtgatgcc cttagatgtt ctgggccgca cgcgcgctac 1440
actgatgggt tcatcgggtt ttaattyyrw ttttatggaa ttgagtgctt ggtcggaagg 1500
cctggctaat ccttggaacg ctcatcgtgc tggggctaga tttttgcaat tattaatctc 1560
caacgaggaa ttcctagtaa acgcaagtca tcagcttgca ttgaatacgt ccctgccctt 1620
tgtacacacc gcccgtcgca cctaccgatt gaacggtccg atgaaaccat gggatgtttc 1680
tgtttggatt vatttttgga cagaggcaga actcgggtga atcttattgt ttagaggaag 1740
gtgaagtcgt aacaagg                                                 1757

SEQ ID NO: 3          moltype = DNA  length = 22
FEATURE              Location/Qualifiers
misc_feature         1..22
                     note = PB00020 Forward primer
source               1..22
                     mol_type = other DNA
                     organism = synthetic construct
SEQUENCE: 3
aacctggttg atcctgccag ta                                             22

SEQ ID NO: 4          moltype = DNA  length = 25
FEATURE              Location/Qualifiers
misc_feature         1..25
                     note = PB00021 Reverse primer
source               1..25
                     mol_type = other DNA
                     organism = synthetic construct
SEQUENCE: 4
ccttgttacg acttcacctt cctct                                          25

SEQ ID NO: 5          moltype = DNA  length = 3327
FEATURE              Location/Qualifiers
misc_feature         1..3327
                     note = nucleotide sequence of the transforming DNA
                      contained in plasmid pPB0128
source               1..3327
                     mol_type = other DNA
                     organism = synthetic construct
SEQUENCE: 5
ggatcccttc tttctttcag cctttgctgg actccctcgc acgcctcctt cttccccagc   60
catccatcag cgggcactcc acccgcgctt caacgctcgc tcgagtgcgt gcttatttgc  120
cttcaacgcg gcgcggcggt taatatagtc ccagcactcc ttaagggggg catcgcaggg  180
attatctttt caaaacctgt cacggagtta catcttccct cgcatcaaag tgttcccggc  240
cgcgtcgcac atctcagttt tataacctac acccctggtg gggtaggggc gaattctatg  300
tacacagcac ctcagaactt gcgcgcgttc cgcgacaaat gagggggtgtg gcggcgcatt  360
cggccgcatc gccacattca gatatctaac ataccccccc ttcgcgatga gtggcaggcg  420
aggcggattc gctcgcgaga ggcgaggtgc cacagcagac cagtaacgag gagccaaggt  480
aggtgaccac cgacgactac gaccacgacc acgaccacga ccacagccac ggcggctgca  540
gccacgggac gcctcgcatg gcagcgcagc agcatcagca acgacagctg caaggagcgc  600
agggccgatc tggacgcgcc ggagccgcac gaccaatgcc gacgcaacgc tgattcttct  660
ggattccctc tatacatgca tatatatatg cagagaagcg gatgaaatgg cctgcgaata  720
```

-continued

```
aatgaatggc ttggagtttg cttgccgtat gctcgaaagt gcgtgtgtag acacaggcac  780
gaccgagagg acaacagtct gtgcttacct caccagcaca ttcttgcaac gccatacgaa  840
gcacgcgaaa ttttgtggct cagagcaaaa ggcattcgtg gtacgggaac gtggggaacg  900
ctatcaattt ggaattcaaa atgagtgaac cagacaacta actgtgactt gaactgttgc  960
tccacgcatc aaaaccaaac ccttaacaga agtagaccag ttcaaagcta ctagcaccaa  1020
acaaaatgat tgaacaagat ggattgcacg caggttctcc ggccgcttgg gtggagaggc  1080
tattcggcta tgactgggca caacagacaa tcggctgctc tgatgccgcc gtgttccggc  1140
tgtcagcgca ggggcgcccg gttctttttg tcaagaccga cctgtccggt gccctgaatg  1200
aactgcagga cgaggcagcg cggctatcgt ggctggccac gacgggcgtt ccttgcgcag  1260
ctgtgctcga cgttgtcact gaagcgggaa gggactggct gctattgggc gaagtgccgg  1320
ggcaggatcc cctgtcatct caccttgctc ctgccgagaa agtatccatc atggctgatg  1380
caatgcggcg gctgcatacg cttgatccgg ctacctgccc attcgaccac caagcgaaac  1440
atcgcatcga gcgagcacgt actcggatgg aagccggtct tgtcgatcag gatgatctgg  1500
acgaagagca tcaggggctc gcgccagccg aactgttcgc caggctcaag gcgcgcatgc  1560
ccgacggcga ggatctcgtc gtgacccatg gcgatgcctg cttgccgaat atcatggtgg  1620
aaaatggccg cttttctgga ttcatcgact gtggccggct gggtgtggcg gaccgctatc  1680
aggacatagc gttggctacc cgtgatattg ctgaagagct tggcggcgaa tgggctgacc  1740
gcttcctcgt gctttacggt atcgccgctc ccgattcgca gcgcatcgcc ttctatcgcc  1800
ttcttgacga gttcttctga gatccgcgc tggctacgca ccagtcctcg attgccacac  1860
cgcccacatt gcctgcaagt tcgccgagat ccagaacaag atggaccgtc gttccggtaa  1920
gatccttgag gatgccccca gttcatcaa gtccggtgac tccgccatgg tcaagatgat  1980
cccctccaag aagatgtgcg ttgagtcctt cactgagtac cctcccctcg gcgcttcgc  2040
cgtccgtgac atgcgtgtca ccgtcgccgt cggtgtcatc aaggaggttg agaagggtga  2100
caagtaagtg gtttgacctc ttatacttga tcgaaatact acctacactt aacctttttt  2160
gcgatttat cgtgattagt ttgctttttc ttgattcgtt tctattcttc caaagttgtg  2220
tcgaccgtc gtattgtgtt gattattccg caggctggtt gtatcttgtt atcatatttt  2280
ttcttgaaag tcgttgaagt ccgcggttct gccatttcct atggaggtgt tttgttatga  2340
agctaggatg taagtttctt gtttttgtagt gttgtcttga aagagttaag cttttaattt  2400
tagtatgttt tagagattga ttcagcatgg atattcagga tagtgtactt gatggtacaa  2460
tcgttgttaa tggttcgtcg tctgtttta taatttaaag atttgacatg tcggaaaagg  2520
tcacaacaga tggagtcccc cgattttgga gtggttgttg gagatttggg cattttttaga  2580
tgattttttt ttctgtgttc tgctacgctg ttgcatacac ttgcttatgt ttaagattga  2640
tgcttgtaag ataccagggt tgattgagat agctctagat gtttattat ggtattaggt  2700
attgtgaact acgaaatcat tgatgtttga aaatatacta acgtttctac tgtaaaacat  2760
gatggttata ggtctctaag aaaataggtt tatggtatat taagcgatgg ataaaatttg  2820
tttaagagga aagtattcga tatcgcaact gtgtcgatca acgatgggca aagaatctat  2880
tcgctaaatc aaaaacctat cctgtctgtc gttggcgtgc gaccaagaag cacgggttcg  2940
gcagcaggta ctgtttggag ctcgagaaga gcttagtaaa cgctgaggtg cctccatcgt  3000
gggagccatc agagagattt ctgctgcttc actttcgttg gaaagtgagg tgaaccatct  3060
gttcgatacc tggaccacaa cgtgagtgg gaaacagtct tgctttgagg cagtttgcag  3120
ccgcttagat tttttagatt ttggtaaagt tcgaagagga catttgactg gttttgtctc  3180
atagcttgtt ttctttacag aacaacacta ctcattgatt taaagcggtg cgaacgaatt  3240
tcaattgatt cgctgcattc tatttcatat cagttaaaat gggtagcgac aataaccgat  3300
cgcgggtaga aaacctgcca aggatcc                                       3327
```

```
SEQ ID NO: 6              moltype = DNA  length = 1599
FEATURE                  Location/Qualifiers
misc_feature             1..1599
                         note = nucleotide sequence of PB31 codon-optimized S.
                          cerevisiae SUC2 gene (ScSUC2) in plasmid pPB0136
source                   1..1599
                         mol_type = other DNA
                         organism = synthetic construct
SEQUENCE: 6
atgcttcttc aagcatttct ttttcttctt gctggttttg ctgctaagat ttctgcttct  60
atgacaaacg agacatctga tcgccctctt gttcatttta cacctaacaa gggttggatg  120
aacgatccta acggtctttg gtacgatgag aaggatgcta agtggcatct ttactttcaa  180
tacaacccta acgatacagt ttggggtaca cctctttttt ggggtcatgc tacatctgat  240
gatcttacaa actgggagga tcaacctatt gctattgtct ctaagcgcaa cgattctggt  300
gcttttctg gttctatggt tgttgattac aacaacacat ctggtttttt taacgataca  360
attgatcctc gccaacgctg cgttgctatt tggacataca acacacctga gtctgaggag  420
caatacattt cttactctct tgatggtggt tacacattta ctgagtacca aaagaaccct  480
gttcttgctg ctaactctac acaatttcgc gatcctaagg ttttttggta cgagccttct  540
caaaagtgga ttatgacagc tgctaagtct caagattaca agattgagat ttactcttca  600
gatgatctta agtcttggaa gctcgagtct gcttttgcta cgagggtttt cttggttatc  660
caatacgagt gccctggtct tattgaggtt cctactgagc aagatccttc taagtcttac  720
tgggttatgt ttatttctat taaccctggt gctcctgctg gtggctcttt taaccaatac  780
tttgttggtt cttttaacgg tacacatttt gaggcttttg ataaccaatc tcgcgttgtt  840
gattttggta aggattacta cgctcttcaa acatttttta acacagatcc tacatacggt  900
tctgctcttg gtattgcttg ggcttctaac tgggagtact ctgcttttgt tcctacaaac  960
ccttggcgct cttctatgtc tcttgttcgc aagtttctc ttaacacaga gtaccaagct  1020
aaccctgaga cagagcttat taaccttaag gctgagccta ttcttaacat ttctaacgct  1080
ggtccttggt ctcgctttgc tacaaacaca acacttacaa aggctaactc ttacaacgtt  1140
gatctttcta actctacagg ttacacttga tttgagcttg tttacgctgt taacacaca  1200
caaacaattt ctaagtctgt ttttgctgat ctttctcttt ggtttaaggg tcttgaagat  1260
cctgaggagt accttcgcat gggttttgag gtttctgctt cttcttttttt tcttgatcgc  1320
ggtaactcta aggttaagtt tgttaaggag aaccttact ttacaaaccg catgtctgtt  1380
aacaaccaac ctttaagtc tgagaacgat ctttcttact acaaggttta cggtcttctt  1440
gatcaaaaca ttcttgagct ttactttaac gatggtgatg ttgtttctac aaacacatac  1500
```

-continued

```
tttatgacta caggtaacgc tcttggttct gttaacatga caacaggtgt tgataaccttt   1560
ttttacattg ataagtttca agttcgcgag gttaagtaa                            1599

SEQ ID NO: 7               moltype = DNA   length = 375
FEATURE                    Location/Qualifiers
misc_feature               1..375
                           note = nucleotide sequence of PB31 codon-optimized S.
                            hindustanus bleomycin resistant gene in plasmid pPB0240
source                     1..375
                           mol_type = other DNA
                           organism = synthetic construct
SEQUENCE: 7
atggctaagc ttacatctgc tgttcctgtt cttacagctc gcgatgttgc tggtgctgtt   60
gagtttggga cagatcgcct tggttttct  cgcgattttg ttggatga tttttgctggt    120
gttgttcgcg atgatgttac acttttatt  tctgctgttc aagatcaagt tgttcctgat   180
aacacacttg cttgggtttg ggttcgcggt cttgatgagc tttacgctga gtggtctgag   240
gttgtttcta caaactttcg cgatgcttct ggtcctgcta tgacagagat tggtgagcaa   300
ccttgggtc gcgagtttgc tcttcgcgat cctgctggta actgcgttca ttttgttgct    360
gaggagcaag attaa                                                     375

SEQ ID NO: 8               moltype = DNA   length = 3965
FEATURE                    Location/Qualifiers
misc_feature               1..3965
                           note = nucleotide sequence of the transforming DNA
                            contained in plasmid pPB0152
source                     1..3965
                           mol_type = other DNA
                           organism = synthetic construct
SEQUENCE: 8
ggatcccacc tgtttctacc aggaacctga cccttaggt  tttggggtag gcatgcgcta   60
gtggtgtttg ttagttgggg attgtttcga aaagaggtgc tttcaaatga tatgtatata   120
tataatatat tcattcatgt atgtttgaa  atacctagca cttttgaaaa gcgagttgtt   180
agtgaatcgt ctattgttgg cagaaggaca aggcctgagc agaaagaaga aggcagcaaa   240
tccaaatcga acgggatttg acggaaagga gtcgcgcaga gctcgcactc cgacgttgct   300
tttcaaggaa acggctgtac gcagcacaag acacaagtcc agacagccag acgcagcaga   360
caggactcgc tcagcctccc agaattagag gcagtcgcac cttgtttcga tccctccctc   420
ccctcctctc cccagggaac acatacctcg tcggtgtgtt tctctgtatc atctctttct   480
ctcctgacca gcttctactt ctacttctgt agaaagcagc agcactagtg caatcttcaa   540
aagcacagct cagctagcga caagaagaag aagaagatct cttcttgatc ctgctgcctg   600
ctgtggaacg accggcacat atatacataa cttttcattc gttcctttgc acaacttgcc   660
ggaatttgcg gacttcactg accgcgacaa ccaagtctcg tgccgtaaat ctttctacgc   720
agctcctcct tcttcattgc aacaggcggc ggctctcctc tgatccccc  agtccttgtc   780
gttgtacaaa gaaaacatca gaagaagagc attctacaga agaagaaaag aagatcttca   840
ttgttgaaaa accataacca tgattgaaca agatggattg cacgcaggtt ctccggccgc   900
ttgggtggag aggctattcg gctatgactg ggcacaacag acaatcggct gctctgatgc   960
cgccgtgttc cggctgtcag cgcagggggcg cccggttctt tttgtcaaga ccgacctgtc   1020
cggtgccctg aatgaactgc aggacgaggc agcgcggcta tcgtggctgg ccacgacggg   1080
cgttccttgc gcagctgtgc tcgacgttgt cactgaagcg ggaagggact ggctgctatt   1140
gggcgaagtg ccggggcagg atctcctgtc atctcacctt gctcctgccg agaaagtatc   1200
catcatggct gatgcaatgc ggcggctgca tacgcttgat ccggctacct gcccattcga   1260
ccaccaagcg aaacatcgca tcgagcgagc acgtactcgg atggaagccg gtcttgtcga   1320
tcaggatgat ctggacgaag agcatcaggg gctcgcgcca gccgaactgt tcgccaggct   1380
caaggcgcgc atgcccgacg gcgaggatct cgtcgtgacc catggcgatg cctgcttgcc   1440
gaatatcatg gtggaaaatg gccgcttttc tggattcatc gactgtggcc ggctgggtgt   1500
ggcggaccgc tatcaggaca tagcgttggc tacccgtgat attgctgaag agcttggcgg   1560
cgaatgggct gaccgcttcc tcgtgcttta cggtatcgcc gctcccgatt cgcagcgcat   1620
cgccttctat cgccttcttg acgagttctt ctgaagatcc gcgctggcta cgcaccagtc   1680
ctcgattgcc acaccgccca cattgcctgc aagttcgccg agatccagaa caagatggac   1740
cgtcgttccg gtaagatcct tgaggatgcc cccaagttca tcaagtccgg tgactccgcc   1800
atggtcaaga tgatcccctc caagaagatg tgcgttgagt ccttcactga gtaccctccc   1860
ctcggccgct tcgccgtccg tgacatgcgt gtcaccgtcg ccgtcggtgt catcaaggag   1920
gttgagaagg gtgacaagta agtggtttga cctcttatac ttgatcgaaa tactacctac   1980
acttaacctt ttttgcgatt ttatcgtgat tagtttgctt tttcttgatt cgtttctatt   2040
cttccaaagt tgtgtcgacc cgtcgtattg tgttgattat tccgcaggct ggttgtatct   2100
tgttatcata ttttttcttg aaagtcgttg aagtccgcgg ttctgccatt tcctatggag   2160
gtgtttgtt  atgaagctag gatgtaagtt tcttgttttg tagtgttgtc ttgaaagagt   2220
taagctttta attttagtat gttttagaga ttgattcagc atggatattc aggatagtgt   2280
acttgatggt acaatcgttg ttaatggttc gtcgtctgtt tttataattt aaagatttga   2340
catgtcggaa aaggtcacaa cagatggagt cccccgattt tggagtggtt gttggagatt   2400
ttggcatttt tagatgatt  ttttttctgt gttctgctac gctgttgcat acacttgctt   2460
atgtttaaga ttgatgcttg taagatacca gggttgattg agatagctct agatgtttat   2520
ttatggtatt aggtattgtg aactacgaaa tcattgatgt ttgaaaatat actaacgttt   2580
ctactgtaaa acatgatggt tataggtctc taagaaaata ggtttatggt atattaagcg   2640
atggataaaa tttgtttaag aggaaagtat tcgatatcgc aactgtgtcg atcaacgatg   2700
ggcaaagaat ctattcgcta aatcaaaaac ctatcctgtc tgtcgttggc gtgcgaccaa   2760
gaagcacggg ttcggcagca ggtactgttt ggagctcgag aagagcttag taaacgctga   2820
ggtgcctcca tcgtgggagc catcagagag atttctgctg cttcactttc gttggaaagt   2880
ggagtgaacc atctgttcga tacctggacc acaacgtgag ttgggaaaca gtcttgcttt   2940
gaggcagttt gcagccgctt agattttta gattttggta aagttcgaag aggacatttg    3000
```

-continued

```
actggttttg tctcatagct tgttttcttt acagaacaac actactcatt gatttaaagc  3060
ggtgcgaacg aatttcaatt gattcgctgc attctatttc atatcagtta aaatgggtag  3120
cgacaataac cgatcgcggg tagaaaacct gccaattcag acaagtccgt gcccagcttt  3180
gacctccttc gctatgcccc ggtgtccttc ccgctcattt tcatgaccca gatggcaaac  3240
tacatgcgtg ttctcgagct cctcggaacc tcgcatgaaa aggtgccca gcagggttgg  3300
ttcaagggcg ctctcggcca cagccagggc gttgtggctg ctgccgtcac tgctgccgca  3360
tccaccgatc gcgagcttcg caacctctcc gtcgcaggcc ttgagttcat gtcccaaatt  3420
ggtcttggcg cccagaagag catgaacttc gagctctcac gccgctccgc aggacccgag  3480
tccccatgc tgtccgtgca aggcatgagc gaggctaccc ttctcaaggc cttcaaggag  3540
gccaccaagc ttgccgtaca aaaagagacc atgatggcca agttctccac atcctccaag  3600
gacgacaagg ctgccccgaa tgcttcgcag cgtcttggta ttgccctgtg caacggcaca  3660
gacgactatg tggtctgtgg cgagcccaag gacctccgca tgctgcgcaa ggtcattgtt  3720
tccatgagcc ccgaggtcgg taaggaggct caggcgcgtg tacccttttc caagcgcaag  3780
cccgtaacgc agacgacatt tcttcgcatg accgcaccct ttcacagtgc tcttaacgca  3840
gaggcatttg agcaggtcgc cgcctgggca gccagctcag cctttggtca ggaacttgcg  3900
caaaggactc ttcgcatccc ggtctgggac actgagaagg gcgcagactt gcgaaagatg  3960
gatcc                                                             3965
```

SEQ ID NO: 9                moltype = DNA   length = 3383
FEATURE                     Location/Qualifiers
misc_feature               1..3383
                           note = nucleotide sequence of the transforming DNA
                            contained in plasmid pPB0218
source                     1..3383
                           mol_type = other DNA
                           organism = synthetic construct
SEQUENCE: 9

```
gcggccgcac aaacaaaaca aagcaggaaa gaaagaaaca aacaaatata caaacaaaga   60
aagaaagaag tggtgggaac tagggaaatc aatgtgtttg cttctttcgc acctttgctt  120
ttcttgcttt tcttggttct caagtaagcg tttatcgcgc cctcagaaaa caaaataaaa  180
tgatctaaca taacatgaat ttatatttat tttatttgtt tattaaataa atgtttttg  240
taaaccagaa tttcactcta cttttgcaac actgagagag tgccatctgc ataataagtg  300
gcagtgtttt tttgtttatt ttcaaattaa ttatacttga actgctaggt caagaggccg  360
cagcggcctg atgagataag gacagagtag gcaaggatgg cagaagatcg cgaaaaaagc  420
gggaaaggca aacgagcagg cccgaaggtg aggtggagct gcttgtcaag gtcgcgaggt  480
ttgtttgaca gttataacag caagaactaa ggcaatttca agaatgaaga gcactcgaat  540
aaaccgatga agcaaagtgt gtacatacaa acatacatac gtacgatga aaagaacaga  600
ttttcaataa aaatgacttt ttagtttaaa caatgtttct gtttgttgtt tcgctttca  660
ttaatttgtt gcaaattatt ttgtttttgt ttttgttttt gttttttgaa atcataaaag  720
agatgctgcc gcagacgtct gcgcgtctca tagttgattg ggtaatcgtt ttgttgagtt  780
ttgaaaatgt aaacttcact tagttgctca tttatcctca ttcgtttgcc catttgttct  840
ctgtttgaag cagagttttg acttctcgca ttcgtggaat ccaccccttg cttgctttgc  900
ttgcttgctt gcctgcttgc tttgcttgct tgcttgacca gcgtgcgcgc tttgccagc  960
ctagccttcg agacctcttg aagacccttt ggagcgtcta gttcgaggtt ctttctattt  1020
gcttcaagag agacaaaata acaaagaaaa agagagaaaa aacaagcaaa gaaagaaaca  1080
aggaaacaaa ccacaaagca cgcatcgtgc atccaaactt tcatcccccc actctctctc  1140
tctctctctc tctctctcct tcctcggaaa aggagtgaga caaaggcaga cagcctctag  1200
cttggcagcc tcgcagctcg tgcggcgcca gttcctacag cttcgcgctg tccaaacgcc  1260
agtccatcgc agcttcggct agctagttgg ctgattgatt gattgattga ttgattgata  1320
gcctttatta cggcgttgat taactgattg attatttgat tgctctggca tccctgtaat  1380
cacttgctca aggtaatcaa tcacatcatt tatacatctc ctccaaagca aaccatctac  1440
acgaccgctt tttgatcgat ctaaaagtgc cggtcaggtg acacgcaagc tcttttttg  1500
tttacagtaa gcagcaacaa gaaagcaaaa agatgattga acaagatgga ttgcacgcag  1560
gttctccggc cgcttgggtg gagaggctat tcggctatga ctgggcacaa cagacaatcg  1620
gctgctctga tgccgccgtg ttccggctgt cagcgcaggg gcgcccggtt ctttttgtca  1680
agaccgacct gtccggtgcc ctgaatgaac tgcaggacga ggcagcgcgg ctatcgtggc  1740
tggccacgac gggcgttcct tgcgcagctg tgctcgacgt tgtcactgaa gcgggaaggg  1800
actggctgct attgggcgaa gtgccgggc aggatctcct gtcatctcac cttgctcctg  1860
ccgagaaagt atccatcatg gctgatgcaa tgcggcggct gcatacgctt gatccggcta  1920
cctgcccatt cgaccaccaa gcgaaacatc gcatcgagcg agcacgtact cggatggaag  1980
ccggtcttgt cgatcaggat gatctggacg aagagcatca ggggctcgcg ccagccgaac  2040
tgttcgccag gctcaaggcg cgcatgcccg acggcgagga tctcgtcgtg acccatggcg  2100
atgcctgctt gccgaatatc atggtggaaa atggccgctt ttctggattc atcgactgtg  2160
gccggctggg tgtggcggac cgctatcagg acatagcgtt ggctacccgt gatattgctg  2220
aagagcttgg cggcgaatgg gctgaccgct tcctcgtgct ttacggtatc gccgctcccg  2280
attcgcagcg catcgccttc tatcgccttc ttgacgagtt cttctgaagg ccaataggac  2340
gcccaagccg aacagtagca acacctggaa gtccctgcag ccacccttc cttcatctg  2400
gaggactagc cacacgaccc tagatataat ggcctctcgc aagaatgtga gcgctgctca  2460
cgaaatgcac gacgagaagc gcattgccgt ggtgggcatg gccgtgcaat acgcgggcta  2520
caaagacaag gaagagttct ggaaagtagt catgggcggt gaggctgcat ggactaagat  2580
tagcgataaa cgcctcggat ccaacaagcg agccgagcac ctcaaagcag agcgtagcaa  2640
atttgcagat accttttgca acgagaacta cggctgcgtc gatgactccg tcgataacga  2700
acacgagctt ctccttaagc tctccaagaa ggctctctcc gagacatcgg tctccgactc  2760
tacaaggtgc ggtattgtga gcggatgcct gtcctttcgc atggacaacc tccagggcag  2820
actcctcaat gtgtaccaaa accacgtcga aaagaaactc ggcgctcgcg tcttcaagga  2880
tgcctccaag tggtccgagc gtgagcagtc gcagaacccc gaggctggtg accgccgcat  2940
ctttatggac ccggcatcct tcgtagcaga agagctcaac ctcggtcctc ttcactactc  3000
tgtcgatgct gcctgtgcca ccgcccttta cgtccttcgc ctcgcccagg accacctcgt  3060
ttctggtgct gctgatgtca tgctcgctgg tgcaacttgc ttcccggagc cctttctcac  3120
```

-continued

```
cctctccgga ttctccactt tccaggccat gcctgtatcg ggagacggca tctcgtaccc   3180
gcttcacaag gacagtcagg gtctcacccc tggtgaaggt ggtgccatta tggttctcaa   3240
gcgccttgac gacgctattc gcgatggaga ccacatttac ggtactctgc tcggtgctac   3300
catcagcaat gctggctgtg gtcttcccct caagccgcac ttgcccagcg agaagtcctg   3360
cctcattgat acctagcggc cgc                                          3383

SEQ ID NO: 10             moltype = DNA  length = 3073
FEATURE                   Location/Qualifiers
misc_feature              1..3073
                          note = nucleotide sequence of the transforming DNA
                           contained in plasmid pPB0258
source                    1..3073
                          mol_type = other DNA
                          organism = synthetic construct
SEQUENCE: 10
gcggccgcca aatcaattag cagtctatcg tgatattagt tagtaactaa caaactaaca   60
aacagataaa cagacaaaca gacaaacaaa caaaacaaac aaaacaaaca aaacaaacaa   120
aacaaagcaa gaaagaaaga aacaaacaaa tatacaaaca aagaaagaaa gaagtggtgg   180
gaactaggga aatcaatgtg tttgcttctt tcgcaccttt gcttttcttg cttttcttgg   240
ttctcaagta agcgtttatc gcgccctcag aaaacaaaat aaaatgatct aacataacat   300
gaatttatat ttattttatt tgtttattaa ataaatgttt tttgtaaacc agaatttcac   360
tctacttttg caacactgag agagtgccat ctgcataata agtggcagtg tttttttgtt   420
tattttcaaa ttaattatac ttgaactgct aggtcaagag gccgcagcag cctgatgaga   480
taaggacaga gtaggcaagg atggcagaag atcgcgaaaa aagcgagaaa ggcaaacgag   540
caggcccgaa ggtgaggtgg agctgcttgt caaggtcgcg aggtttgttt gacagttata   600
acagcaagaa ctaaggcaat ttcaagaatg aagagcactc gaataaaccg atgaagcaaa   660
gtgtgtacat acaaacatac atacgtacag atgaaaagaa cagattttca ataaaaatga   720
cttttttagtt taaacaatgt ttctgtttgt tgtttcgctt ttcattaatt tgttgcaaat   780
tattttgttt ttgtttttgt ttttgttttt gaaaatcata aaagagatgc tgccgcagac   840
gtctgcgcgt ctcatagttg attgggtaat cgttttgttg agttttgaaa atgtaaactt   900
cacttagttg ctcatttatc ctcattcgtt tgcccatttg ttctctgttt gaagcagagt   960
tttgacttct cgcattcgtg gaatccaccc cttgcttgct ttgcttgctt gcttgcctgc   1020
ttgctttgct tgcttgcttg accagcgtgc gcgcttttgc cagcctagcc ttcgagacct   1080
cttgaagacc ctttggagcg tctagttcga ggttctttct atttgcttca agagagacaa   1140
aataacaaag aaaagagag aaaaaacaag caaagaaaga aacaaggaaa caaaccacaa   1200
agcacgcatc gtgcatccaa actttcatcc ccccactctc tctctctctc tctctctctc   1260
cttcctcgga aaaggagtga gacaaaggca gacagcctct agcttggcag cctcgcagct   1320
cgtgcggcgc cagttcctac agcttcgcgc tgtccaaacg ccagtccatc gcagcttcgg   1380
ctagctagtt ggctgattga ttgattgatt gattgattga ttgattgata gcctttatta   1440
cggcgttgat taactgattg attatttgat tgctctggca tccctgtaat cacttgctca   1500
aggtaatcaa tcacatcatt tatacatctc ctccaaagca aaccatctac acgaccgctt   1560
tttgatcgat ctaaaagtgc cggtcaggtg acacgcaagt tcttttttg tttacagtaa   1620
gcagcaacaa gaaagcaaaa agatggctaa gcttacatct gctgttcctg ttcttacagc   1680
tcgcgatgtt gctggtgctg ttgagttttg gacagatcgc cttggttttt ctcgcgattt   1740
tgttgaggat gattttgctg gtgttgttcg cgatgatgtt acacttttta tttctgctgt   1800
tcaagatcaa gttgttcctg ataacacact tgcttgggtt tgggttcgcg gtcttgatga   1860
gctttacgct gagtggtctg aggttgtttc tacaaacttt cgcgatgctt ctggtcctgc   1920
tatgacagag attggtgagc aaccttgggg tcgcgagttt gctcttcgcg atcctgctgg   1980
taactgcgtt cattttgttg ctgaggagca agattaaagg ccaataggac gcccaagccg   2040
aacagtagca acacctggaa gtccctgcag ccacccctttc cttcatctgg gaggactagc   2100
cacacgaccc tagatataat ggcctctcgc aagaatgtga gcgctgctca cgaaatgcac   2160
gacgagaagc gcattgccgt ggtgggacatg gccgtgcaat acgcgggctg caaagacaag   2220
gaagagttct ggaaagtagt catgggcggt gaggctgcat ggactaagat tagcgataaa   2280
cgcctcggat ccaacaagcg agccgagcac ctcaaagcag agcgtagcaa atttgcagat   2340
acctttgca acgagaacta cggctgcgtc gatgactccg tcgataacga acacgagctt   2400
ctccttaagc tctccaagaa ggctctctcc gagacatcgg tctccgactc tacaaggtgc   2460
ggtattgtga gcggatgcct gtcctttccc atggacaacc tccagggcga actcctcaat   2520
gtgtaccaaa accacgtcga aaagaaactc ggcgctcgcg tcttcaagga tgcctccaag   2580
tggtccgagc gtgagcagtc gcagaacccc gaggctggtg accgccgcat ctttatggac   2640
ccggcatcct tcgtagcaga agagctcaac ctcggtcctc ttcactactc tgtcgatgct   2700
gcctgtgcca ccgcccttta cgtccttcgc ctcgcccagg accacctcgt ttctggtgct   2760
gctgatgtca tgctcgctgg tgcaacttgc ttcccggagc cctttctcac cctctccgga   2820
ttctccactt tccaggccat gcctgtatcg ggagacggca tctcgtaccc gcttcacaag   2880
gacagtcagg gtctcacccc tggtgaaggt ggtgccatta tggttctcaa gcgccttgac   2940
gacgctattc gcgatggaga ccacatttac ggtactctgc tcggtgctac catcagcaat   3000
gctggctgtg gtcttcccct caagccgcac ttgcccagcg agaagtcctg cctcattgat   3060
acctagcggc cgc                                                     3073
```